(12) United States Patent
Yada et al.

(10) Patent No.: US 7,288,169 B2
(45) Date of Patent: Oct. 30, 2007

(54) DISTILLATION APPARATUS FOR READILY POLYMERIZABLE COMPOUND

(75) Inventors: Shuhei Yada, Mie (JP); Yasushi Ogawa, Mie (JP); Yoshiro Suzuki, Mie (JP); Kenji Takasaki, Mie (JP); Kiyoshi Takahashi, Mie (JP)

(73) Assignee: Mitsubishi Chemical Corporation, Tokyo (JP)

( * ) Notice: Subject to any disclaimer, the term of this patent is extended or adjusted under 35 U.S.C. 154(b) by 64 days.

(21) Appl. No.: 10/781,986

(22) Filed: Feb. 20, 2004

(65) Prior Publication Data

US 2004/0222077 A1 Nov. 11, 2004

Related U.S. Application Data

(63) Continuation of application No. PCT/JP02/08428, filed on Aug. 21, 2002.

(30) Foreign Application Priority Data

| Aug. 22, 2001 | (JP) | 2001-251067 |
| Nov. 27, 2001 | (JP) | 2001-360436 |
| Dec. 4, 2001 | (JP) | 2001-370271 |
| Dec. 27, 2001 | (JP) | 2001-397463 |
| Jan. 11, 2002 | (JP) | 2002-004318 |

(51) Int. Cl.
*B01D 3/10* (2006.01)
*B01D 3/42* (2006.01)

(52) U.S. Cl. ............ 202/158; 202/160; 202/161; 202/162; 202/205

(58) Field of Classification Search ............ 202/158, 202/160–162, 205; 203/1–2, 8, 91, DIG. 14, 203/DIG. 21; 562/600
See application file for complete search history.

(56) References Cited

U.S. PATENT DOCUMENTS

| 3,988,213 A | * | 10/1976 | Yoshida et al. ............ 203/9 |
| 4,142,491 A | | 3/1979 | Hibino et al. |
| 5,143,585 A | * | 9/1992 | Ichikawa et al. ............ 203/2 |
| 5,702,504 A | * | 12/1997 | Schaub et al. ............ 95/101 |
| 5,856,562 A | | 1/1999 | Mine et al. |
| 6,267,848 B1 | * | 7/2001 | Popov ............ 203/91 |
| 6,280,578 B1 | * | 8/2001 | Popov ............ 203/91 |

(Continued)

FOREIGN PATENT DOCUMENTS

CN 1263787 8/2000

(Continued)

*Primary Examiner*—Virginia Manoharan
(74) *Attorney, Agent, or Firm*—Oblon, Spivak, McClelland, Maier & Neustadt, P.C.

(57) ABSTRACT

A distillation apparatus for subjecting a crude readily polymerizable compound to distillation under vacuum conditions to purify the same includes a distillation column and a vacuum generator, an exhaust gas conduit of the vacuum generator being connected to a connecting conduit therebetween through a pressure control valve. The purification method includes using the disclosed distillation apparatus and controlling the action of the pressure control valve based on a pressure of the distillation column, thereby controlling the amount of the exhaust gas to be introduced to control the pressure of the distillation column.

14 Claims, 13 Drawing Sheets

U.S. PATENT DOCUMENTS

| | | |
|---|---|---|
| 6,348,134 B1 * | 2/2002 | Popov .................. 196/114 |
| 6,348,135 B1 * | 2/2002 | Nakahara et al. ............ 203/8 |
| 6,398,918 B1 * | 6/2002 | Popov .................... 203/2 |
| 6,596,129 B1 * | 7/2003 | Yoneda et al. ............. 203/2 |
| 6,632,329 B1 * | 10/2003 | Mizutani et al. ........... 203/1 |
| 6,676,808 B2 * | 1/2004 | Hamamoto et al. .......... 203/8 |
| 6,755,943 B1 * | 6/2004 | Mizutani et al. ........... 203/99 |
| 6,878,239 B1 * | 4/2005 | Matsumoto et al. ......... 203/8 |

FOREIGN PATENT DOCUMENTS

| | | |
|---|---|---|
| CN | 1269351 | 10/2000 |
| CN | 1287994 | 3/2001 |
| CN | 1294028 | 5/2001 |
| CN | 1142002 C | 3/2004 |
| CN | 1561251 | 1/2005 |
| EP | 0 827 765 A2 | 8/1998 |
| EP | 1 029 572 A2 | 8/2000 |
| EP | 1 029 573 A2 | 8/2000 |
| EP | 1 057 804 A2 | 12/2000 |
| EP | 1 095 685 A1 | 5/2001 |
| JP | 60-222105 | 11/1985 |
| JP | 7-53449 | 2/1995 |
| JP | 9-316026 | 12/1997 |
| JP | 10-17524 | 1/1998 |
| JP | 200-256221 | 9/2000 |
| JP | 2000-256258 | 9/2000 |
| JP | 2000-300903 | 10/2000 |
| JP | 2001-131116 | 5/2001 |

* cited by examiner

DISTILLATION APPARATUS FOR READILY POLYMERIZABLE COMPOUND

CROSS REFERENCE TO RELATED APPLICATION

This is a Continuation Application of PCT Application No. PCT/JP02/08428, filed on Aug. 21, 2002, which was not published under PCT Article 21(2) in English. This application is based upon and claims the benefit of priority from the prior Japanese Patent Application Nos. 2001-251067, filed Aug. 22, 2001, 2001-360436, filed Nov. 27, 2001, 2001-370271, filed Dec. 04, 2001, 2001-397463, filed Dec. 27, 2001, and 2002-004318, filed Jan. 11, 2002, the entire contents of which are incorporated herein by reference.

TECHNICAL FIELD

The present invention relates to a distillation apparatus, a production process and a purification method of readily polymerizable compounds. More particularly, the invention relates to a distillation apparatus, a production process, a purification method, etc., which are improved for preventing plugging of the distillation apparatus, etc. and continuing the production stably over a long period of time, in the case of producing readily polymerizable compounds, especially (meth)acrylic acid, (meth)acrylic acid esters, etc.

BACKGROUND ART

Acrylic acid is, for example, produced in the following process. That is, first of all, propane or propylene as the starting material is subjected to vapor phase catalytic oxidation, and the resulting oxidation reaction mixture is absorbed in an absorbing solvent such as water, thereby recovering a solution of acrylic acid. This solution contains various impurities formed as by-products during the vapor phase catalytic oxidation, such as acetic acid, maleic acid, acrolein, furfural, benzaldehyde, and acetone, other than acrylic acid. In a preliminary purification step, the absorbing solvent and a part of the by-products are removed from the resulting acrylic acid solution to obtain crude acrylic acid consisting essentially of acrylic acid and its dimer and other heavy components. Subsequently, the crude acrylic acid is purified in a vacuum distillation column, etc. in a purification step to recover high-purity acrylic acid.

In the production process of an acrylic acid ester, first of all, acrylic acid is reacted with an alcohol in the presence of an acid catalyst, and the resulting reaction mixture is then purified in a vacuum distillation column to recover a high-purity acrylic acid ester.

In the production process of methacrylic acid or a methacrylic acid ester, methacrylic acid or a methacrylic acid ester is, for example, produced in the same process as described above using isobutylene as the starting material.

Hitherto, even though a problem of plugging does not occur in a relatively small-sized distillation column as in experimental equipment, serious plugging may possibly occur in a large-sized distillation column as in commercial equipment. It is considered that this is caused due to the matter that non-uniformity within the column increases with an increase in the instrumental size. For example, even when the degree of horizontality of a distillation column, i.e., the gradient per unit length, is identical, the difference of elevation increases in proportion to the column diameter of the distillation column.

In the case where it is intended to compensate the increase in non-uniformity with an increase in the instrumental size by precision, execution becomes difficult as the instrumental size increases.

In operating a vacuum distillation column of readily polymerizable compounds, a pressure control valve is plugged due to polymerization in a condensate, resulting in a problem such that it becomes impossible to control the degree of vacuum in the distillation column within a fixed range.

In a tray of a distillation apparatus, in the case where an acrylic acid-containing liquid is passed through pores provided on a weir-free perforated tray and flown down (see JP-A-2000-300903, etc.), a part of the liquid travels on the inner wall of the pore and goes around into the back face of the perforated tray, and the resulting liquid becomes one of the factors to form a polymer, causing a matter that long-term continuous production of (meth)acrylic acids cannot be carried out.

In continuously operating a distillation column, it is the most problematic that a differential pressure within the distillation column, namely a difference between the column bottom pressure and the column top pressure increases. The elevation of the differential pressure within the column is caused by the matter that the pore size on the perforated tray is reduced by the polymer, whereby both a liquid and a gas become to hardly flow. When accumulation of the polymer advances, some pores are completely plugged. Ultimately, both the liquid and the gas cannot sufficiently flow, whereby the operation of the distillation column is unavoidably stopped.

Also, the production equipment of (meth)acrylic acid, etc. includes column equipment such as a distillation column of crude (meth)acrylic acid, etc. or a decomposition reaction column of decomposing high-boiling materials to recover (meth)acrylic acid, etc. In the column equipment, an introducing tubular member in which a part of the column bottom liquid is introduced into a reboiler and heated, and then returned to the column bottom is provided connecting to the bottom face of the lower end of the column.

According to the conventional connection structure of the tubular member for introducing a column bottom liquid to the reboiler, polymers, a polymerization inhibitor and others contained in the column bottom liquid are liable to incorporate into the introducing tubular member. And the polymers and polymerization inhibitor accumulate in the reboiler, thereby possibly causing plugging. Incidentally, the polymerization inhibitor is added in the production step of readily polymerizable compounds. The polymers include ones carried from the equipment in the upstream side and ones formed within the column equipment.

With respect to a countermeasure against the plugging, in the case where a pump for forced circulation is provided in the introducing tubular member, it is known to provide a strainer in the introducing tubular member, thereby separating the polymers and polymerization inhibitor by filtration. However, if the opening of the strainer is made large, the separation by filtration becomes insufficient so that an effect for preventing plugging of the reboiler is insufficient. Conversely, if the opening of the strainer is made small, clogging of the strainer frequently occurs so that the works of the column equipment likely become instable. Incidentally, in a spontaneous circulation type reboiler, such a strainer cannot be placed, and a measure for preventing inflow of the polymers and polymerization inhibitor into the reboiler is not employed.

For the sake of preventing polymerization of a readily polymerizable compound within an instrument, the following countermeasures have hitherto been employed, for example. That is, a chemical countermeasure is to delay or retard polymerization reaction of acrylic acid with an initiator as a radical, in which a polymerization inhibitor of capturing the radical is, for example, added to the absorbing solvent or in the preliminary purification step or purification step, or the operating temperature is lowered for the purpose of delaying the radical formation. As the polymerization inhibitor of acrylic acid, gaseous materials such as oxygen and a variety of organic or inorganic compounds are known. Concretely, p-hydroquinone, p-methoxyphenol, phenothiazine, and others are known. Usually, in many cases, oxygen and an organic or inorganic compound are used jointly. For the sake of lowering the operating temperature, an operation pressure of the distillation operation is lowered.

In the case where an organic or inorganic compound is used as the polymerization inhibitor, such a compound is in general used as a solution thereof. For example, JP-A-10-17524 describes that a solution prepared by dissolving a copper compound such as copper carbonate and copper hydroxide and hydroquinone as polymerization inhibitors in an acetic acid aqueous solution obtained in distilling off water from a (meth)acrylic acid solution by dehydration distillation in a preliminary purification step is used. Though the polymerization inhibitor solution obtained by such a method has excellent performance, there is involved a problem such that the acetic acid component to be removed in the preliminary purification step is carried into the system, thereby increasing a purification load in the preliminary purification step.

A physical or mechanical countermeasure is to prevent the generation of polymerization due to local deviations in formulation, flow rate, residence time, temperature, and others. For example, it is achieved by reducing the residence of the liquid or gas by changing the instrumental shape or by lowering the roughness of the instrument surface.

However, as described previously, the serious plugging problem in a large-sized distillation column as in the commercial equipment has not been solved yet.

A problem of the invention is to solve the serious plugging problem in a large-sized distillation column as in the commercial equipment and to provide an apparatus and a method for distilling and purifying a readily polymerizable compound stably over a long period of time. In more detail, the following points are enumerated.

A first problem of the invention is to provide a process of producing a purified readily polymerizable compound, wherein in distilling and purifying a readily polymerizable compound, an improvement is made such that plugging of a pressure control valve is prevented and the readily polymerizable compound carried in an exhaust gas of a vacuum generator can be easily recovered.

A second problem of the invention is to enable one to control inflow of polymers or polymerization inhibitor into a reboiler by a simple mechanism, thereby making it possible to continuously operating column equipment stably over a long period of time.

A third problem of the invention is to provide a perforated tray capable of preventing occurrence of polymerization of a (meth)acrylic acid when it goes around into the back face of the tray and a process of producing a (meth)acrylic acid using the same.

A fourth problem of the invention is to provide a method of distilling (meth)acrylic acid in which by preventing plugging of an opening of a weir-free perforated tray by polymer and preventing elevation of a differential pressure within a column, a (meth)acrylic acid solution can be distilled stably over a long period of time.

A fifth problem of the invention is to provide a process of producing (meth)acrylic acid in which a purification load is reduced in a preliminary purification step.

DISCLOSURE OF THE INVENTION

In order to solve the foregoing problems, the present inventors made extensive and intensive investigations. As a result, first of all, they have found a distillation apparatus comprising a distillation column and a vacuum generator and an exhaust gas conduit of the vacuum generator connected to a connecting conduit therebetween through a pressure control valve and that a pressure of the distillation column is controlled by adjusting the amount of the exhaust gas to be introduced using the distillation apparatus.

Secondly, they have found distillation equipment having a column main body and a reboiler into which a column bottom liquid of the column main body is introduced through an introducing tubular member, the introducing tubular member connecting to the side face of the column main body. In such an invention, the tubular member for introducing the column bottom liquid into the reboiler connects laterally. Since the polymers and polymerization inhibitor contained in the column bottom liquid incline to flow downward in the vertical direction, they hardly incorporate into the introducing tubular member. For that reason, according to the invention, the amounts of the polymers and polymerization inhibitor flowing into the reboiler through the introducing tubular member become small, whereby plugging in the reboiler is prevented.

In the invention, it is preferable that the introducing tubular member is horizontal or ascends toward the downstream side in the vicinity of the upstream end of the introducing tubular member, namely in the vicinity of a place where the introducing tubular member connects to the column main body, its pot part or a discharging tubular member. Thus, the amounts of the polymers and polymerization inhibitor flowing into the introducing tubular member become smaller, whereby plugging in the reboiler is prevented more surely.

Thirdly, they have found a perforated tray in which not only a number of pores penetrating from the upper face of the tray to the back face thereof are provided, but also a surrounding projection wall hanging down from the back face of the tray is provided in the outer periphery of the lower end of the pore.

Fourthly, they have found that alignment of openings of a weir-free perforated tray of a distillation column having a large column diameter is made uniform, the flow rate dropping along an edge of the opening is increased, and a proper amount of oxygen is made co-present within the column.

Fifthly, they have found that a polymerization inhibitor solution is prepared using waste water containing (meth)acrylic acid generated in a vacuum source in a preliminary purification step and/or purification step of (meth)acrylic acid and then fed into the collection step or subsequent steps thereto.

The invention has been completed based on the foregoing knowledge.

Specifically, a first aspect of the invention is concerned with a distillation apparatus for subjecting a crude readily polymerizable compound to distillation under vacuum conditions to purify it, the distillation apparatus being characterized by comprising a distillation column and a vacuum generator and an exhaust gas conduit of the vacuum generator connected to a connecting conduit therebetween through a pressure control valve.

A second aspect of the invention is concerned with a method of purifying of a readily polymerizable compound by subjecting a crude readily polymerizable compound to distillation under vacuum conditions to purify it, the method being characterized by using a distillation apparatus comprising a distillation column and a vacuum generator and an exhaust gas conduit of the vacuum generator connected to a connecting conduit therebetween through a pressure control valve and controlling the action of the pressure control valve based on a pressure of the distillation column, thereby controlling the amount of the exhaust gas to be introduced to control the pressure of the distillation column.

A third aspect of the invention is concerned with column equipment for treating a readily polymerizable compound having a column main body and a reboiler into which a column bottom liquid of the column main body is introduced through an introducing tubular member, the column equipment being characterized in that the introducing tubular member connects to the side face of the column main body.

A fourth aspect of the invention is concerned with a method of distilling (meth)acrylic acid by distilling a (meth) acrylic acid solution using a distillation column in which at least a part of trays is a weir-free perforated tray, the method being characterized in that openings of the weir-free perforated tray are positioned on respective intersections of an oblique lattice comprising a first group of lines aligned in parallel and at even intervals and a second group of lines oblique to the first group of lines and aligned in parallel and at even intervals; with respect to a local opening rate (B/A) that is a ratio of a sum B of areas of openings of a region comprising of a parallelogram surrounded by the oblique lattice to an area A of the region and a ratio u/S of a total area u of all of the openings to a column sectional area S, a value of (u/S)/(B/A) ratio is 0.67 or more; the flow rate dropping along an edge of the opening is 0.035 m³/m·h or more; the distillation column has a column diameter of 1.2 m or more; and an oxygen concentration in a gas within the column is from 0.008 to 0.1% by mole.

A fifth aspect is concerned with a process of producing (meth)acrylic acid through respective steps of a collection step of bringing a reaction product gas containing (meth) acrylic acid obtained by vapor catalytic oxidation reaction into contact with an aqueous absorbing liquid to absorb the (meth)acrylic acid in the gas into the absorbing liquid, a preliminary purification step of removing the absorbing liquid and impurities from the resulting (meth)acrylic acid solution to obtain crude (meth)acrylic acid, and a purification step of obtaining purified (meth)acrylic acid from the crude (meth)acrylic acid by purification including distillation of (meth)acrylic acid by vacuum distillation, the process being characterized in that a polymerization inhibitor solution is prepared using waste water containing (meth)acrylic acid generated in a vacuum source in the preliminary purification step and/or purification step and then fed into the collection step or subsequent steps thereto.

A sixth aspect is concerned with a perforated tray for distillation column, which is characterized in that a number of pores penetrating from the upper face of a tray to the back face thereof are provided, and a surrounding projection wall hanging down from the back face of the tray is provided in the outer periphery of the lower end of the pore.

A seventh aspect is concerned with a process of producing a (meth)acrylic acid by using a distillation column including a perforated tray provided with a number of pores penetrating from the upper face of the tray to the back face thereof and with a surrounding projection wall hanging down from the back face of the tray in the outer periphery of the lower end of the pore.

Figure 1:
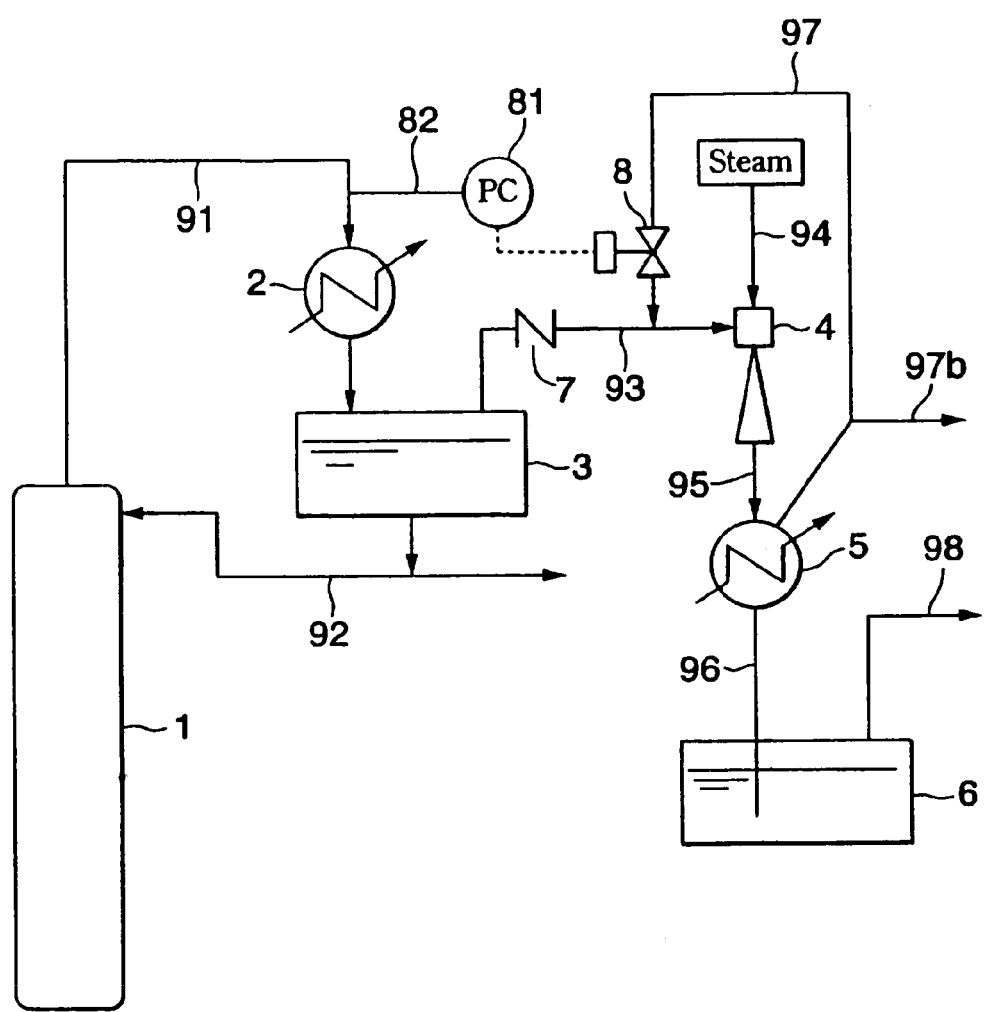
FIG. 1 is an explanatory drawing to show one example of a distillation apparatus to be used in the production process of the invention.

Incidentally, with respect to the reference numerals in the drawings, 1 is a distillation column; 2 is a condenser; 21 is a condenser; 3 is a reflux tank; 4 is an ejector; 5 is a condenser; 6 is a liquid seal tank; 7 is a check valve; 8 is a pressure control valve; 81 is a pressure controller; 82 is a detection pipe; 97 is an exhaust gas conduit; 101 is a column main body; 102 is a discharge nozzle; 103 is an introduction nozzle; 105 is a reboiler; 121 is a reflux tank; 131 is a liquid tank; 201 is a distillation column; 202 is a perforated tray; 221 is a pore; 222 is a surrounding projection wall; 203 is a stock liquid feed pipe; 204 is a reboiler; 241 is a vapor inlet pipe; 242 is a liquid outlet pipe; 243 is a bottoms pipe; 205 is a condenser; 251 is a vapor outlet pipe; 252 is a reflux pipe; 253 is a distillate pipe; 301 is a distillation column; 303 is a reboiler; 310 is a weir-free perforated tray; 311 is a first group of lines; 312 is a second group of lines; 313 is an oblique lattice; 315 is an opening; 322 is a reflux tank; A is a collection column; B is a dehydration column; C is a light-boiling removal column; D is a purification column; E is a heat decomposition column; 401 is a reaction product gas introducing pipe; 402 is an absorbing water introducing pipe; 403 is a polymerization inhibitor solution introducing pipe; 404 is a distillate discharge pipe; 405 is a distilled light-boiling fraction discharge pipe; 406 is a purified acrylic acid discharge pipe; 407 is a light-boiling fraction discharge pipe; and 408 is a heavy component discharge pipe, respectively.

BEST MODE FOR CARRYING OUT THE INVENTION

The invention relates to an improved distillation apparatus for distillation and purification of readily polymerizable compounds and a purification method of readily polymerizable compounds using the same. The characteristics thereof reside in a distillation apparatus for subjecting a crude readily polymerizable compound to distillation under vacuum conditions to produce a purified readily polymerizable compound, which is characterized by comprising a distillation column and a vacuum generator and an exhaust gas conduit of the vacuum generator connected to a connecting conduit therebetween through a pressure control valve; and in a method of purifying a readily polymerizable compound, which is characterized in that by using the distillation apparatus, the action of the pressure control valve is controlled based on a pressure of the distillation column, thereby controlling the amount of the exhaust gas to be introduced to control the pressure of the distillation column.

Representative examples of readily polymerizable compound as a subject with which the invention deals include (meth)acrylic acid and (meth)acrylic esters. Incidentally, the (meth)acrylic acid as referred to herein means acrylic acid or methacrylic acid and is sometimes expressed as a (meth) acrylic acid. Examples of acrylic acid esters include methyl acrylate, ethyl acrylate, butyl acrylate, isobutyl acrylate, tertiary butyl acrylate, 2-ethylhexyl acrylate, 2-hydroxyethyl acrylate, 2-hydroxypropyl acrylate, and methoxyethyl acrylate. Examples of methacrylic acid esters include similar compounds thereto.

As the step of producing acrylic acid, for example, the following (1) to (3) are enumerated.

(1) The production includes an oxidation step of subjecting propane, propylene and/or acrolein to catalytic vapor phase oxidation, a collection step of bringing an acrylic acid-containing gas from the oxidation step into contact with water to collect acrylic acid as an acrylic acid aqueous solution, an extraction step of extracting acrylic acid from the acrylic acid aqueous solution using a proper extraction solvent, and a subsequent purification step of separating the acrylic acid from the solvent and then purifying crude acrylic acid and further includes a step in which a high-boiling liquid containing an acrylate Michael adduct and a polymerization inhibitor used in each of the steps is fed as a raw material into a decomposition reaction column to recover a value, and the value is fed into any one of the collection step and subsequent steps thereto.

(2) The production includes an oxidation step of subjecting propane, propylene and/or acrolein to catalytic vapor phase oxidation to produce acrylic acid, a collection step of bringing an acrylic acid-containing gas into contact with water to collect acrylic acid as an acrylic acid aqueous solution, an azeotropic separation step of distilling the acrylic acid aqueous solution in the presence of an azeotropic solvent in an azeotropic separation column and discharging crude acrylic acid from the column bottom, an acetic acid separation step for removing acetic acid, and a purification step for removing high-boiling impurities and further includes a step in which a high-boiling liquid containing an acrylate Michael adduct after the purification and a polymerization inhibitor used in these production steps is fed as a raw material into a decomposition reaction column to recover a value, and the value is fed into any one of the collection step and subsequent steps thereto.

(3) The production includes an oxidation step of subjecting propane, propylene and/or acrolein to catalytic vapor phase oxidation to produce acrylic acid, a collection and separation step of bringing an acrylic acid-containing gas into contact with an organic solvent to collect acrylic acid as an acrylic acid organic solvent solution and simultaneously remove water, acetic acid, etc., and a separation step of discharging crude acetic acid from the acrylic acid organic solvent solution and further includes a step in which a high-boiling liquid containing the polymerization inhibitor, organic solvent and acrylate Michael adduct used in these production steps is fed as a raw material into a decomposition reaction column to recover a value, and the value is fed into any one of the collection step and subsequent steps thereto and a step of purifying a part of the organic solvent.

The step of producing an acrylic acid ester includes, for example, an esterification reaction step of reacting acrylic acid and an alcohol in the presence of an organic acid or a cationic ion exchange resin or the like as a catalyst and a purification step of carrying out extraction, evaporation and distillation as unit operations for concentrating a crude acrylic acid solution obtained in the reaction. Each of the unit operations is properly chosen depending upon a starting material ratio of acrylic acid to the alcohol in the esterification reaction, the kind of the catalyst to be used in the esterification reaction, or physical properties of the respective starting materials, reaction by-products, and acrylic acid esters or others. A product is obtained in a purification column of the acrylic acid ester through the respective unit operations. The column bottom liquid of the purification column is fed as a high-boiling liquid containing a Michael adduct composed mainly of an acrylic acid ester, a $\beta$-acryloxypropionic acid ester, a $\beta$-alkoxyproponic acid ester, and $\beta$-hydroxypropionic acid ester and further containing a polymerization inhibitor used in the production step into a decomposition reaction, or it is returned into the process, thereby recover a value.

Depending upon the kind of the alcohol, there are high-boiling liquids containing as major components acrylic acid, an acrylic acid dimer (hereinafter "dimer"), an acrylic acid trimer (hereinafter "trimer"), a $\beta$-alkoxypropionic acid, and a $\beta$-alkoxypropionic acid ester obtained in any one of the various production steps other than the column bottom of the purification column of the acrylic acid ester product and further containing the polymerization inhibitor used in the production step, and such high-boiling liquids are fed as a high-boiling liquid containing a Michael adduct into the decomposition reaction column to recover a value, and the value is fed into the reaction step or purification step.

With respect to the Michael adduct of acrylic acid or acrylic acid ester as referred to herein, in the case of producing acrylic acid, the Michael adduct includes an acrylic acid dimer (hereinafter "dimer"), an acrylic acid trimer (hereinafter "trimer"), and an acrylic acid tetramer (hereinafter "tetramer"). In the case of producing an acrylic acid ester, the Michael adduct includes a Michael adduct of acrylic acid to the foregoing acrylic acid ester such as alkyl esters or cycloalkyl esters having from 2 to 8 carbon atoms, specific examples of which include a $\beta$-alkoxypropionic acid ester, dimer, trimer, tetramer, esters of trimer, esters of tetramer, $\beta$-hydroxypropionic acid, and a $\beta$-hydroxypropionic acid ester.

As the distillation column of the invention, those generally used in the chemical plant are used.

Trays and packing materials are placed within the column of the distillation column. Concretely, examples of trays include downcomer-provided bubble cap trays, perforated trays, valve trays, Superfrac trays and Max-Frac trays and downcomer-free dual trays.

Examples of packing materials include regular packing materials such as Sulzerpack manufactured by Sluzer Brothers Ltd., Sumitomo Sulzer Packing manufactured by Sumitomo Heavy Industries, Ltd., Melapack manufactured by Sumitomo Heavy Industries, Ltd., Gempak manufactured by Glitsch, Montzpack manufactured by Montz, Good Roll Packing manufactured by Tokyo Special Wire Netting Co., Ltd., Honeycomb Pack manufactured by NGK Insulators, Ltd., Impulse Packing manufactured by Nagaoka Corporation, and MC Pack manufactured by Mitsubishi Chemical Engineering Corporation; and irregular packing materials such as Intalox Saddle manufactured by Norton Company, Tellerette manufactured by Nittetsu Chemical Engineering Ltd., pall ring manufactured by BASF AG, Cascade Mini-Ring manufactured by Mass Transfer Ltd., and Flexiring manufactured by JGC Corporation.

It should not be construed that the invention is limited thereto. Also, the tray and packing material can be used in combination of two or more thereof as in the commonly employed ways.

In the invention, a heat exchange for heating a column bottom liquid attached to each column is defined as a reboiler. In general, though the reboiler is roughly classified into the case where it is placed within the column and the case where it is placed outside the column, the invention is of a subject to one to be placed outside the column.

The model of the reboiler is not particularly limited. Concretely, it includes a vertical fixed tube type, a lateral fixed tube type, a U-shaped tube type, a double tube type, a spiral type, an angular block type, a plate type, and a thin film evaporator type.

The material quality of a variety of nozzles, column main body, reboiler, pipe, etc. in each column is chosen depending upon the readily polymerizable compound to be treated and its temperature condition, but the invention is not particularly limited. For example, in the production of (meth) acrylic acid or (meth)acrylic acid esters representative as the readily polymerizable substance, stainless steels are frequently used, but the invention is limited thereto. For example, SUS304, SUS304L, SUS316, SUS316L, SUS317, SUS317L, SUS327, and Hastelloy are used. These materials may be selected corresponding to the liquid physical properties thereof from the viewpoint of corrosion resistance.

Figure 2:
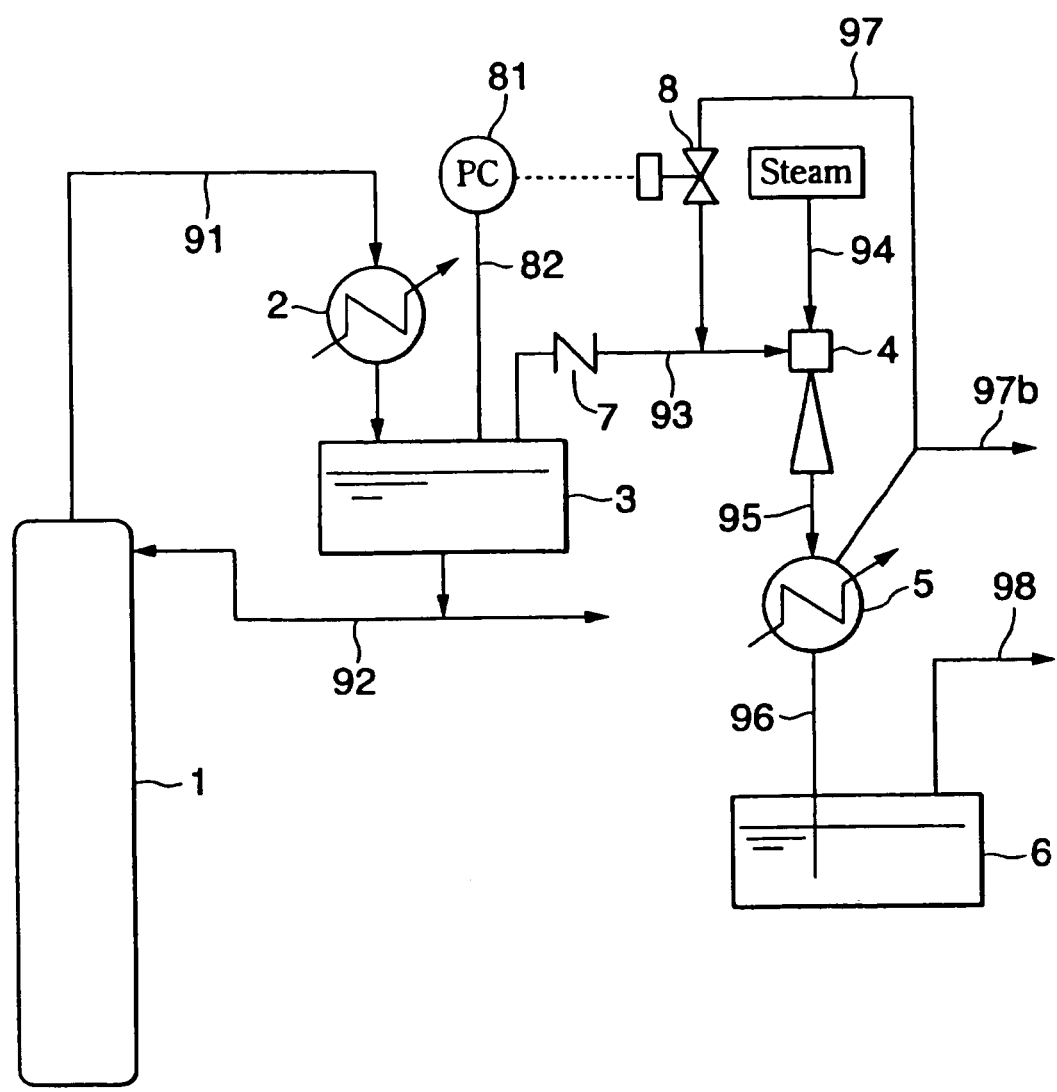
FIG. 2 is an explanatory drawing to show another example of a distillation apparatus to be used in the production process of the invention.
Figure 3:
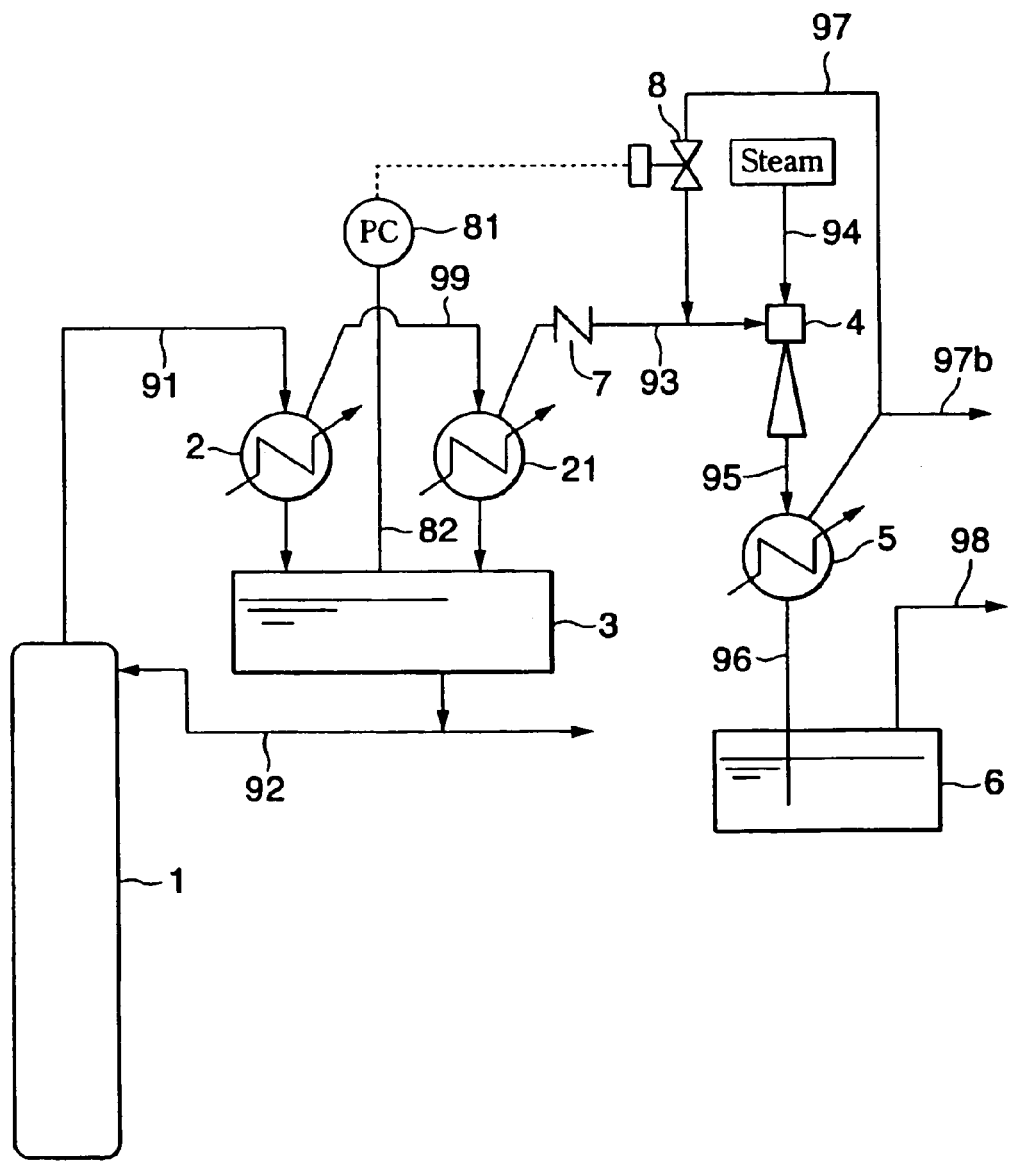
FIG. 3 is an explanatory drawing to shown still another example of a distillation apparatus to be used in the production process of the invention.

The invention will be described below in detail with reference to the accompanying drawings. FIG. 1 is an explanatory drawing to show one example of a distillation apparatus to be used in the process of the invention; FIG. 2 is an explanatory drawing to show another example of a distillation apparatus to be used in the process of the invention; and FIG. 3 is an explanatory drawing to shown still another example of a distillation apparatus to be used in the process of the invention. Incidentally, in the illustrated examples, a steam driving type ejector is used as a vacuum generator.

The method of the invention is a method of distilling a crude readily polymerizable compound under vacuum conditions to purify it. The crude readily polymerizable compound is one obtained as a crude product in the foregoing production process.

Though the purity of the crude (meth)acrylic acid is not particularly limited, it is preferably 85% by weight or more, and more preferably 90% by weight or more. Examples of impurities contained in this crude (meth)acrylic acid include a dimer of (meth)acrylic acid and other heavy components.

As illustrated in the drawings, a condenser (2) and a reflux tank (3) are provided above a distillation column (1). In the case of the distillation apparatus shown in FIGS. 1 and 2, one condenser (2) is provided, and the condenser achieves necessary cooling of a distillate gas from the column top of the distillation column (1). On the other hand, in the case of the distillation apparatus shown in FIG. 3, two condensers (2) and (21) in which vapor phases are connected to each other through a conduit (99) are provided, and the condenser (2) in the high-temperature side achieves cooling of the major part of a distillate gas from the column top of the distillation column (1), whereas the condenser (21) in the low-temperature side achieves cooling of the distillate gas that has not been able to be condensed by the condenser (2). According to such a water recooling system, it becomes possible to reduce a freezing load of the condenser.

The distillate gas from the column top of the distillation column (1) is introduced into the condenser (2) through a conduit (91) and condensed. The resulting condensate is introduced into the reflux tank (3). The condensate in the reflux tank (3) is divided into two parts by a conduit (92), a part of which is circulated as a reflux liquid into the distillation column (1), and the remainder is taken out as a product.

The vapor phase of the reflux tank (3) attached to the distillation column (1) is connected to an ejector (4) through a conduit (93), and the ejector keeps the distillation column (1) in a prescribed vacuum state.

The ejector (4) is provided with a condenser (5) and a liquid seal tank (6) in the downstream thereof. Steam for driving the ejector (4) is introduced through a conduit (94). A vapor discharged from the ejector (4) is introduced into the condenser (5) through a conduit (95) and condensed. The resulting condensate is introduced into the liquid seal tank (6) through a conduit (96). The tip of the conduit (96) is positioned in the liquid of the liquid seal tank (6), whereby liquid seal is achieved. An exhaust gas from the vapor phase of the liquid seal tank (6) is introduced into a combustion furnace (not illustrated) through a conduit (98) and treated.

In the invention, a distillation apparatus comprising an exhaust gas conduit (97) of the ejector (4) connected to the connection conduit (93) between the distillation column (1) and the ejector (4) through a pressure control valve (8) is used. In the case of the illustrated distillation apparatus using a steam driving type ejector, the base end of the exhaust gas conduit (97) of the ejector (4) is connected to the vapor phase of the condenser (5). That is, the exhaust gas of the ejector is taken out from the vapor phase of the condenser (5).

Incidentally, as illustrated in the drawings, a branched exhaust gas conduit (97b) for discharging an oxygen-containing gas (polymerization inhibiting gas) to be introduced into a reboiler (not illustrated) of the distillation column (1) is connected to the exhaust gas conduit (97).

The action of the pressure control valve (8) is specifically carried out based on a signal from a pressure controller (PC) (81). In the case of the distillation apparatus shown in FIG. 1, a detection pipe (82) of the pressure controller (81) is connected to the conduit (91) in the inlet side of the condenser (2), and in the case of the distillation apparatus shown in FIGS. 2 and 3, the detection pipe (82) of the pressure controller (81) is connected to the vapor phase of the reflux tank (3).

In the invention, the detection pipe (82) of the pressure controller (81) is preferably connected to the conduit (91) in the outlet side of the condenser (2) or the vapor phase of the reflux tank (3), and especially preferably connected to the vapor phase of the reflux tank (3). According to such construction, plugging of the detection pipe (82) itself due to polymerization of the condensate of the readily polymerizable compound is prevented.

Also, in the invention, as illustrated in the drawings, it is preferable to provide a check valve (7) in the connection conduit (93) between the distillation column (1) and the ejector (4). The check valve (7) prevents back-flow of the liquid in the liquid seal tank (6) into the reflux tank (3) during stopping of the drive due to a trouble of the ejector (4). In that case, it is preferable that the connection conduit (93) in which the check valve (7) is provided is placed horizontally. According to such construction, the residence of the condensate of the readily polymerizable compound is prevented. As a result, plugging in the check valve (7) due to polymerization of the condensate of the readily polymerizable compound is prevented.

In the invention, using the distillation apparatus thus constructed, the action of the pressure control valve (8) is controlled based on the pressure of the distillation column (1) to adjust the amount of the exhaust gas to be introduced, thereby controlling the pressure of the distillation column (1) within a fixed range. Accordingly, in the pressure control valve (8), the residence of the condensate of the readily polymerizable compound is prevented by the flow of the exhaust gas from the ejector (4), whereby plugging due to the polymerization is prevented. Also, since the readily polymerizable compound-containing exhaust gas from the ejector (4) is utilized, a loss of the readily polymerizable compound is prevented. Further, the polymerizable compound in the exhaust gas from the ejector (4) is recovered in the liquid seal tank (6). Incidentally, the pressure of the distillation column (1) to be controlled is properly chosen as distillation conditions of the crude readily polymerizable compound.

In the invention, as the vacuum generator, in addition to the steam driving type ejector (4) shown in FIGS. 1 to 3, a liquid driving type ejector and a liquid ring vacuum pump can be used. In the case of using a liquid driving type ejector, the condenser (5) is not necessary, and the exhaust gas from the vapor phase of the liquid seal tank (6) is used as the exhaust gas of the vacuum generator. Also, in the case of using a liquid ring vacuum pump, an exhaust gas from the vapor phase of a sealed tank for recovering and circulating a driving liquid (water) is used.

According to the invention as described previously, in the method of distilling a crude readily polymerizable compound under vacuum conditions to purify it, improvements are made such that not only plugging of the pressure control valve can be prevented, but also the readily polymerizable compound carried in the exhaust gas of the vacuum generator can be easily recovered, and an industrial value of the invention is remarkable.

Further, in the invention, by employing a structure having a distillation column main body and a reboiler into which a column bottom liquid of the column main body is introduced through an introducing tubular member, in which the introducing tubular member connects to the side face of the column main body, plugging of the reboiler is prevented, whereby an effect for continuously operating the column equipment stably over a long period of time is enhanced.

Figure 4:
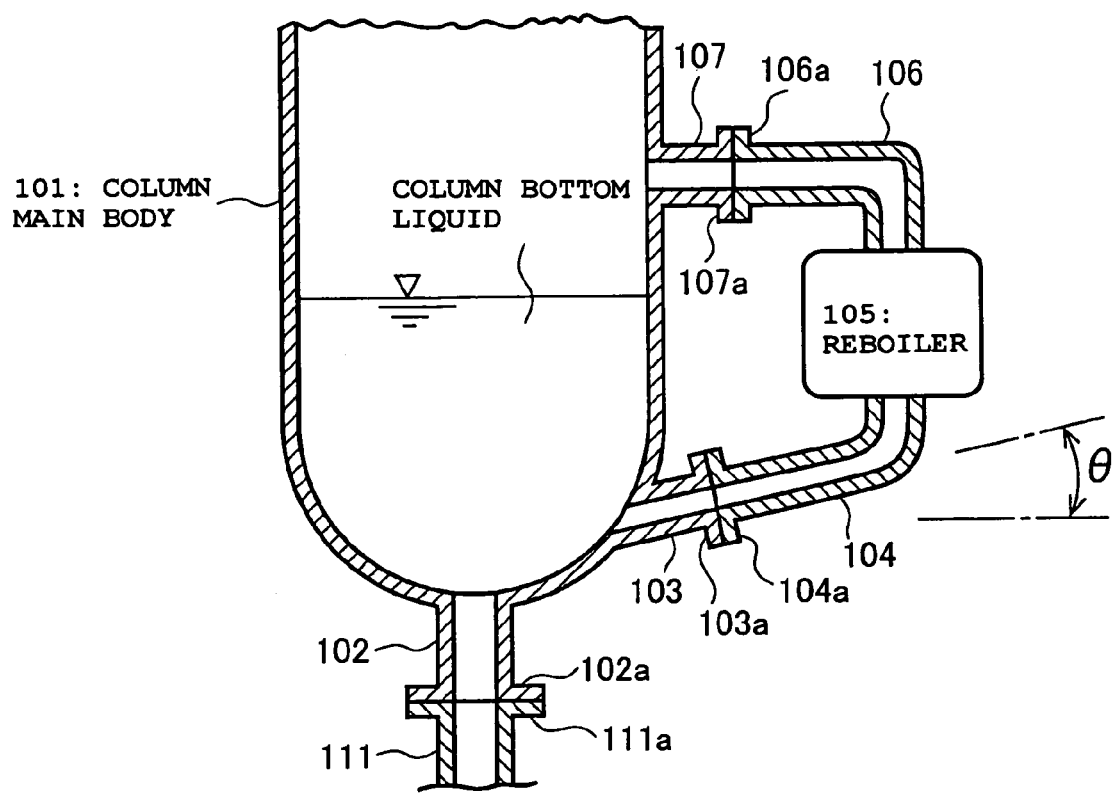
FIG. 4 is a longitudinal sectional view of a lower portion of column equipment of the invention.
Figure 5:
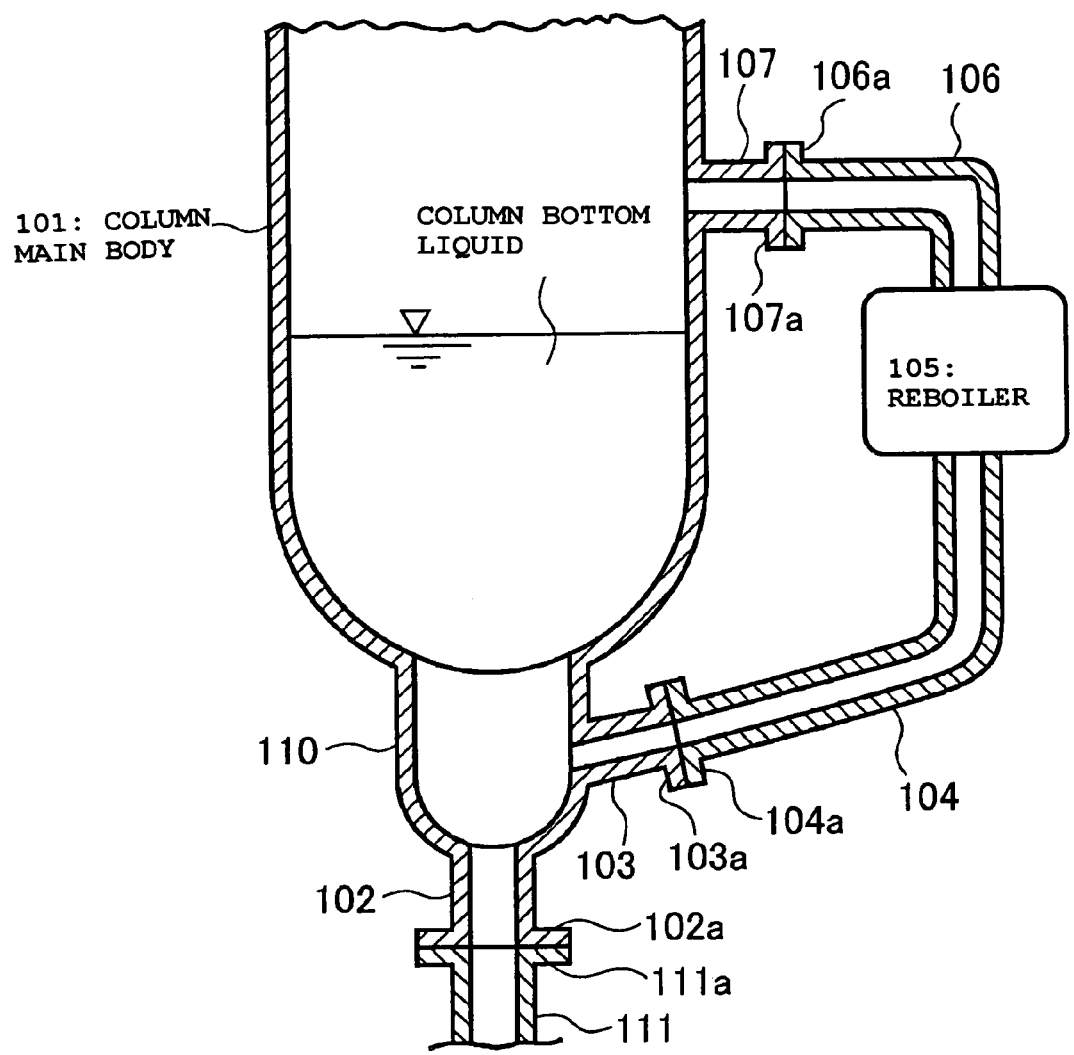
FIG. 5 is a longitudinal sectional view of a lower portion of another column equipment of the invention.
Figure 6:
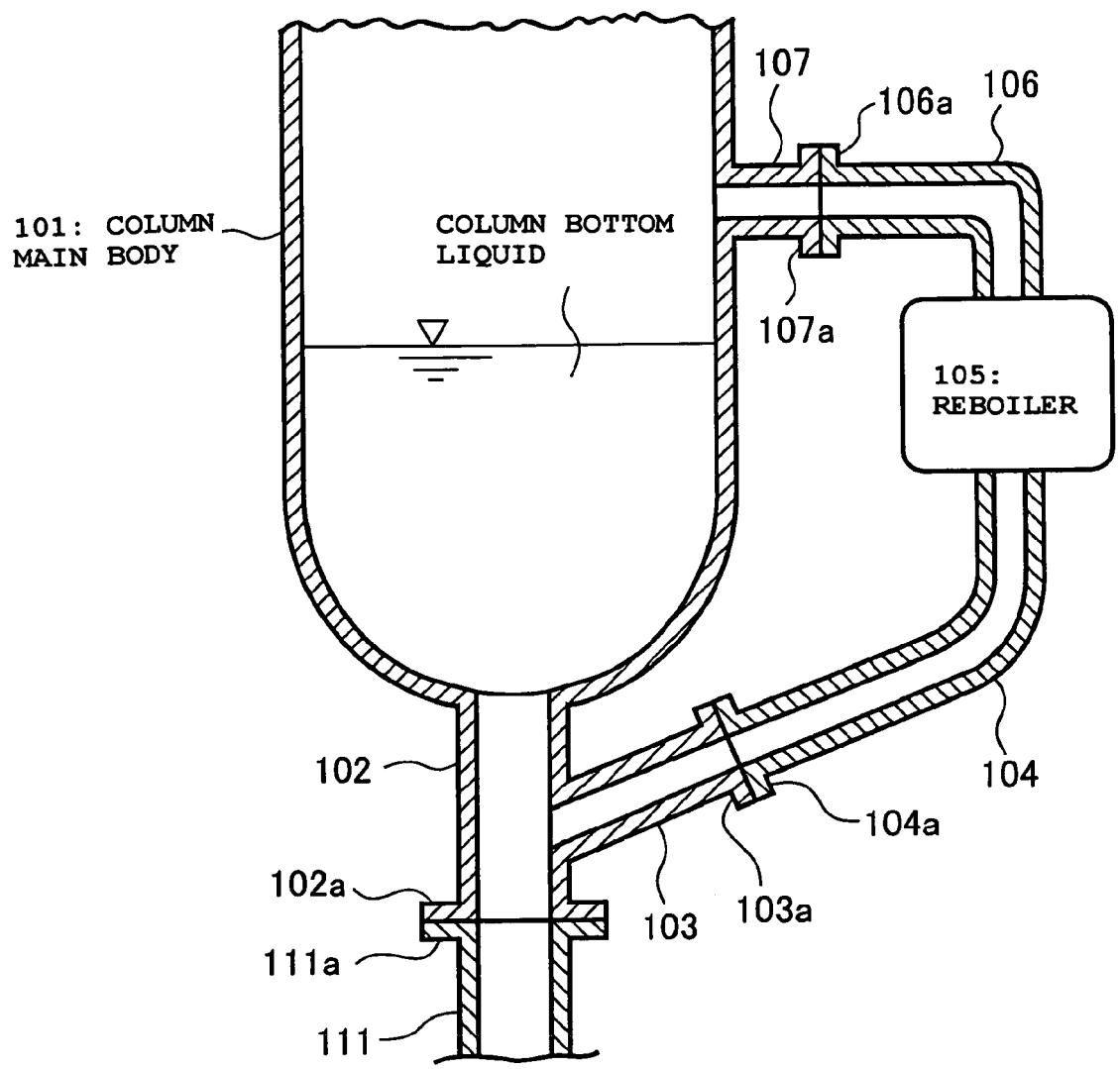
FIG. 6 is a longitudinal sectional view of a lower portion of still another column equipment of the invention.
Figure 7:
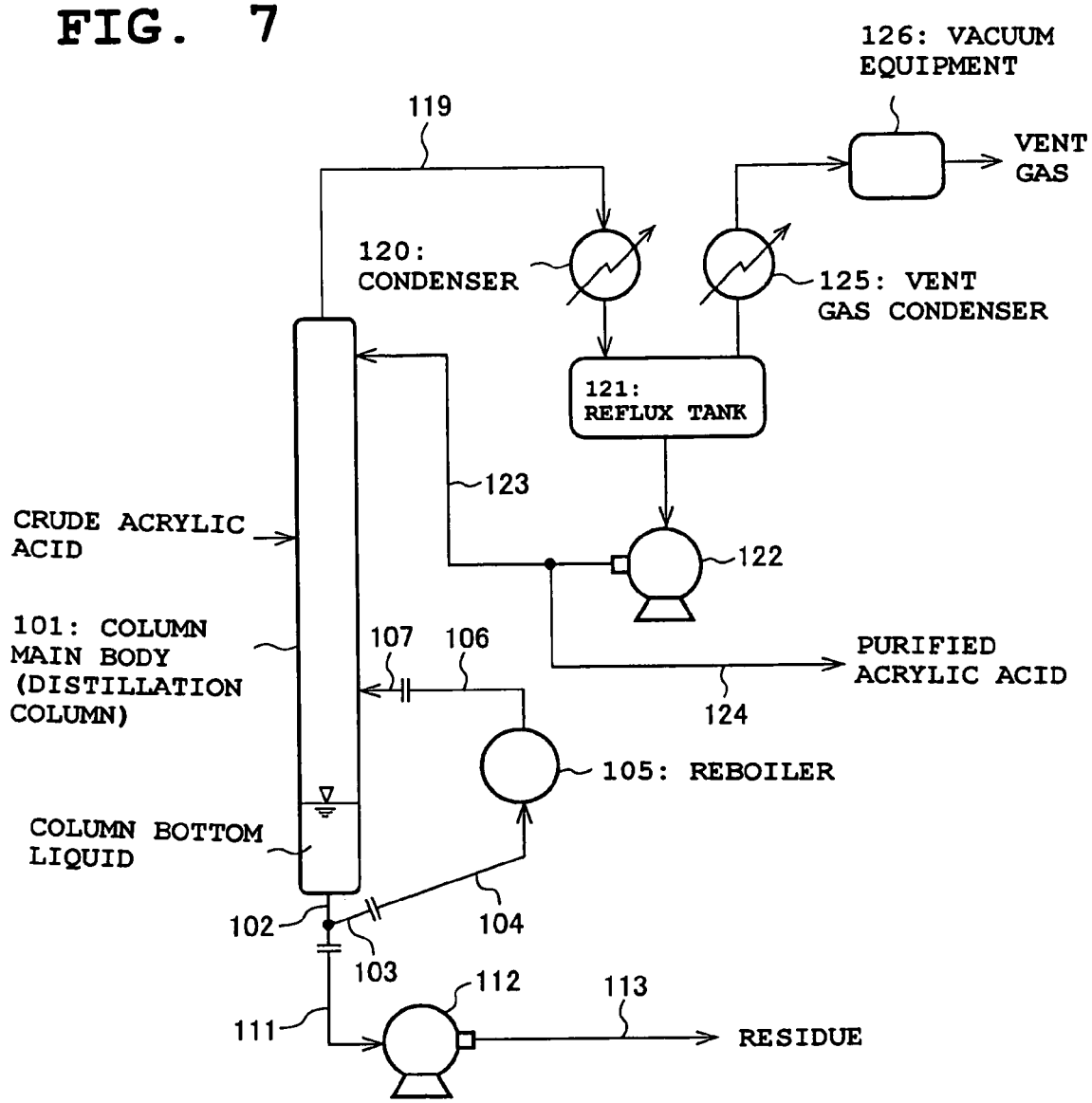
FIG. 7 is a system diagram of a distillation apparatus employing column equipment of the invention.
Figure 8:
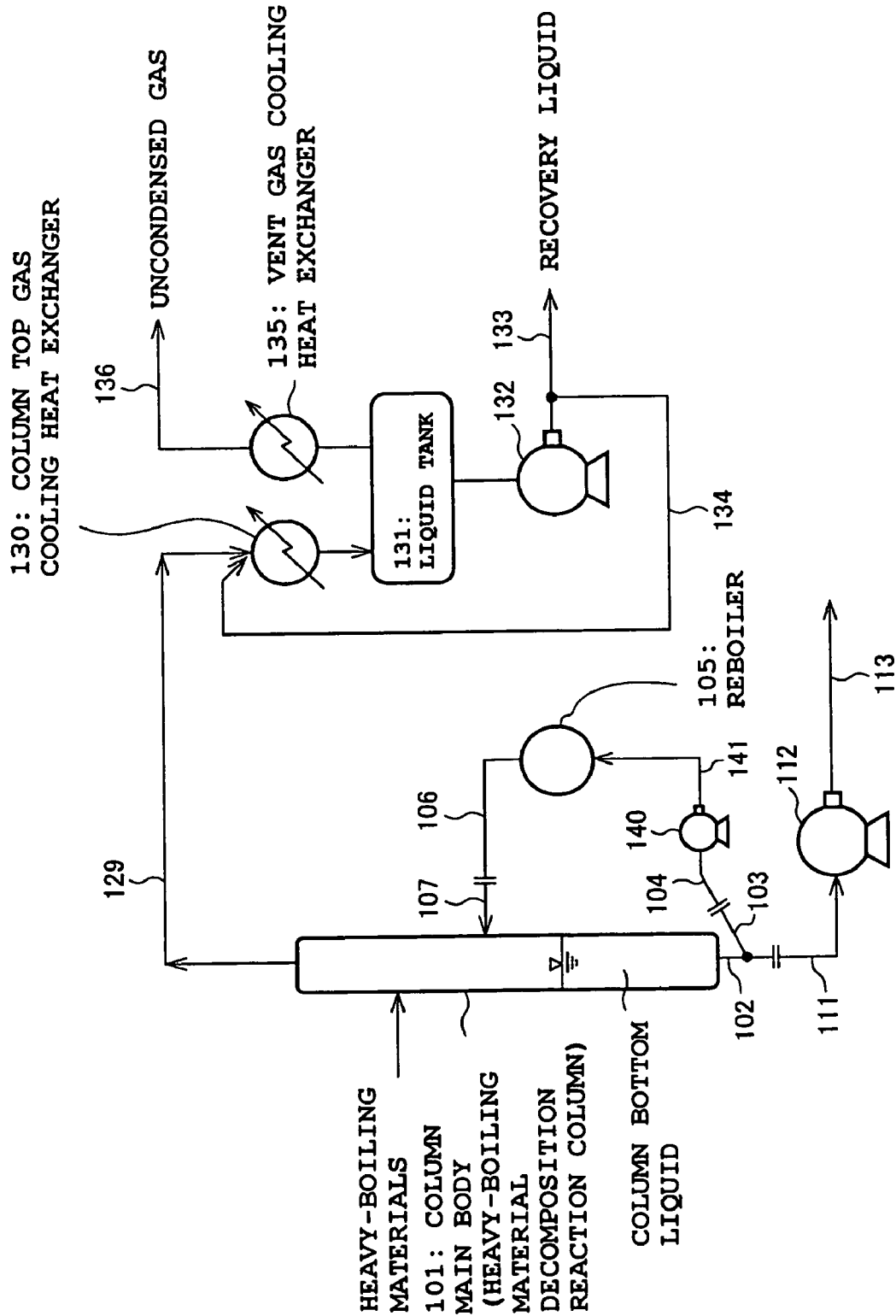
FIG. 8 is a system diagram of a decomposition reaction apparatus of high-boiling materials employing column equipment of the invention.

The invention will be described below with reference to the drawings. FIGS. 4, 5 and 6 are each a longitudinal sectional view in the vicinity of a lower portion of column showing column equipment for readily polymerizable compound relating to embodiment; and FIGS. 7 and 8 are respectively a system diagram of a distillation apparatus and a decomposition reaction apparatus employing the column equipment.

In the column equipment of FIGS. 4, 5 and 6, a column bottom liquid of a column main body 101 is introduced into a reboiler 105 through an introduction nozzle 103 as the introducing tubular member and a conduit 104 and after heating, returned into the column main body 101 through a conduit 106 and a nozzle 107. The nozzle 107 is projected from the column main body 101. The tips in the projection direction of the nozzles 103 and 107 are provided with flanges 103a and 107a, respectively, and flanges 104a and 106a provided in the conduits 104 and 106 are connected to the flanges 103a and 107a, respectively.

In FIGS. 4 and 6, a discharge nozzle 102 as a discharging tubular member is projected downward in the vertical direction from the lower end of the bottom mirror part of the column main body 101. In FIG. 5, the discharge nozzle 102 is projected downward in the vertical direction from the lower end of a pot part 110. A flange 111a of a discharging conduit 111 is connected to a flange 102a provided in the lower end of the discharge nozzle 102.

In the column equipment of FIG. 4, the introduction nozzle 103 is laterally projected from the lower side face of the column main body 101. In the column equipment of FIG. 5, the column main body 101 is provided in the lower end part with the pot part 110 expanding downward, and the introduction nozzle 103 is projected from the side face of the pot part 110. In the column equipment of FIG. 6, the introduction nozzle 103 is projected from the side face of the discharge nozzle 102.

In any of the column equipment, the "vicinity of the upstream end of the discharging tubular member" is constructed of the introduction nozzle 103. This introduction nozzle 103 is provided horizontally or ascending toward the downstream side. That is, the introduction nozzle 103 has an angle (elevation) θ of 0° or more, and preferably from 0 to 85° to the horizontal line against the downstream side (direction toward the reboiler 105).

The length of the introduction nozzle 103 is preferably 0.05 times or more, for example, from 0.08 to 3 times the pipe size (inner diameter, hereinafter the same) of the introduction nozzle 103. When this ratio is less than 0.05, construction of a nozzle is difficult. On the other hand, when it exceeds 3, the projected part from the column main body becomes large, and hence, such is not preferred, too from the standpoint of construction.

Incidentally, in the embodiment of FIG. 6, a ratio (a/b) of the pipe size a of the discharge nozzle 102 to the pipe size b of the introduction nozzle 103 is preferably 0.5 or more, and especially preferably from 0.5 to 2. When the (a/b) is less than 0.5, the solids in the column bottom liquid are liable to be somewhat easily incorporated into the introduction nozzle 103.

In any of the embodiments, since the introduction nozzle 103 is provided horizontally or ascending, the polymers and polymerization inhibitor contained in the column main body 101, pot part 110 or discharge nozzle 102 hardly enter the introduction nozzle 103. Accordingly, it is prevented that these accumulate within the reboiler 105 to cause plugging.

FIG. 7 is a distillation apparatus of acrylic acid employing the column equipment of FIG. 4, and the column main body 101 is used as a distillation column.

Crude acrylic acid is introduced into this distillation column 101 and distilled, and a part of the column bottom liquid is circulated into a discharge nozzle 102, an introduction nozzle 103, a conduit 104, a reboiler 105, a conduit 106, and a nozzle 107 in that order. Also, the column bottom liquid is taken out as a residue through the discharge nozzle 102, the conduit 111, a pump 112, and a conduit 113.

The distillate from the column top is introduced into a reflux tank 121 through a conduit 119 and a condensing condenser 120. A part of acrylic acid in the reflux tank 121 is returned into the column top through a pump 122 and a conduit 123. The remainder of acrylic acid is taken out as purified acrylic acid through a conduit 124 branched from the conduit 123. A gas in the reflux tank 121 is again cooled by a vent gas condenser 125, the condensed acrylic acid is returned into the reflux tank 121, and the gaseous component is taken out as a vent gas through vacuum equipment 126.

Though in FIG. 7, the column equipment of FIG. 6 is employed, it is evident that the column equipment of FIG. 4 or FIG. 5 may be employed. In that case, the construction is the same as in FIG. 7, except that the position of the nozzle 103 is changed to that in FIG. 4 or 5. In any of the cases, the column bottom temperature is preferably from 60 to 120° C., and especially preferably from 70 to 100° C., and the pressure is preferably from 1 to 50 kPa, and especially preferably from 2 to 20 kPa.

In FIG. 8, the column main body 101 is a decomposition reaction column of high-boiling materials generated in the production step of acrylic acid or acrylic acid esters, and the high-boiling materials are introduced into the reaction column 101 and provided for decomposition reaction. A part of the column bottom liquid is returned into the reaction column 101 through a discharge nozzle 102, an introduction nozzle 103, a conduit 104, a pump 140, a reboiler 105, a conduit 106, and a nozzle 107. Also, the column bottom liquid is taken out through a discharge nozzle 102, a conduit 111, a pump 112, and a conduit 113.

The gaseous decomposition product is introduced into a liquid tank 131 from the column top through a conduit 129 and a column top gas cooling heat exchanger 130. The liquid in the liquid tank 131 is taken out as a recovery liquid through a pump 132 and a conduit 133. Incidentally, a part of the column bottom liquid is returned into the heat exchanger 130 through a conduit 134 branched from the conduit 133. The gas in the liquid tank 131 is cooled by a vent gas cooling heat exchanger 135, the condensate is returned into the liquid tank, and an uncondensed gas is taken out through a conduit 136.

Though in FIG. 8, the column equipment of FIG. 6 is employed, the column equipment of FIG. 4 or 5 may be employed. In that case, the construction is the same as in FIG. 8, except that the position of the nozzle 103 is changed to that in FIG. 4 or 5. In any of the cases, the decomposition reaction temperature is preferably from 110 to 250° C., and especially preferably from 120 to 230° C., the decomposition reaction time is preferably from 0.5 to 50 hours (when the decomposition temperature is low, the decomposition reaction time is from 10 to 50 hours, whereas when the decomposition temperature is high, the decomposition reaction time is from 0.5 to 10 hours), and the pressure may be a reduced pressure or atmospheric pressure.

As illustrated in the drawings, in the invention, a pump may be provided in the middle of the introducing tubular member or in the upstream side of the reboiler.

In the invention, by employing a perforated tray for distillation column characterized in that not only a number of pores penetrating from the upper face of the tray to the back face thereof are provided, but also a surrounding projection wall hanging down from the back face of the tray is provided in the outer periphery of the lower end of the pore, formation of polymers on the back face of the tray is effectively prevented, and an effect for continuously operating the distillation column stably over a long period of time is enhanced.

The perforated tray for distillation column and the production process of (meth)acrylic acids according to the invention will be described below with reference to the accompanying drawings.

Figure 9:
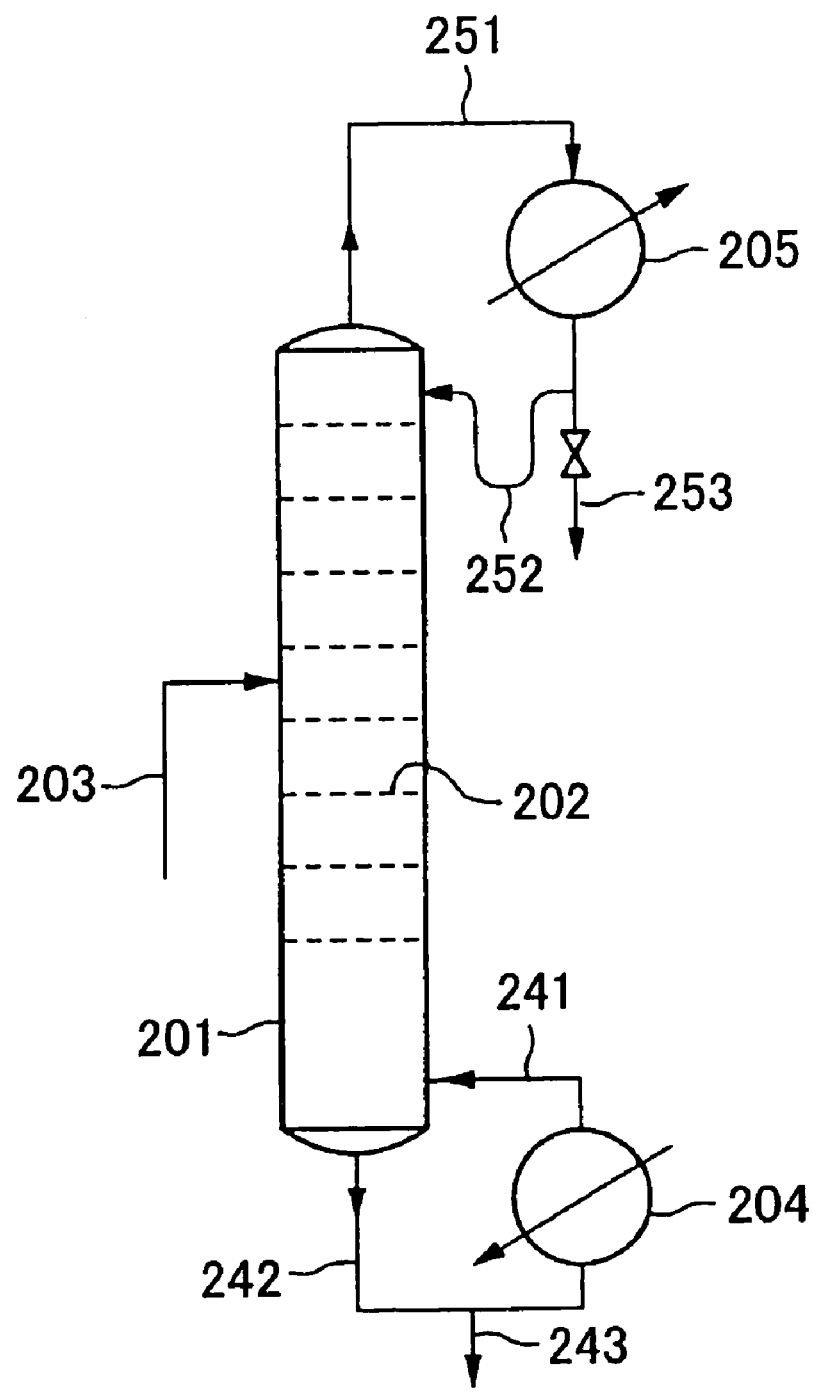
FIG. 9 is a schematic view of a distillation column.
Figure 10:
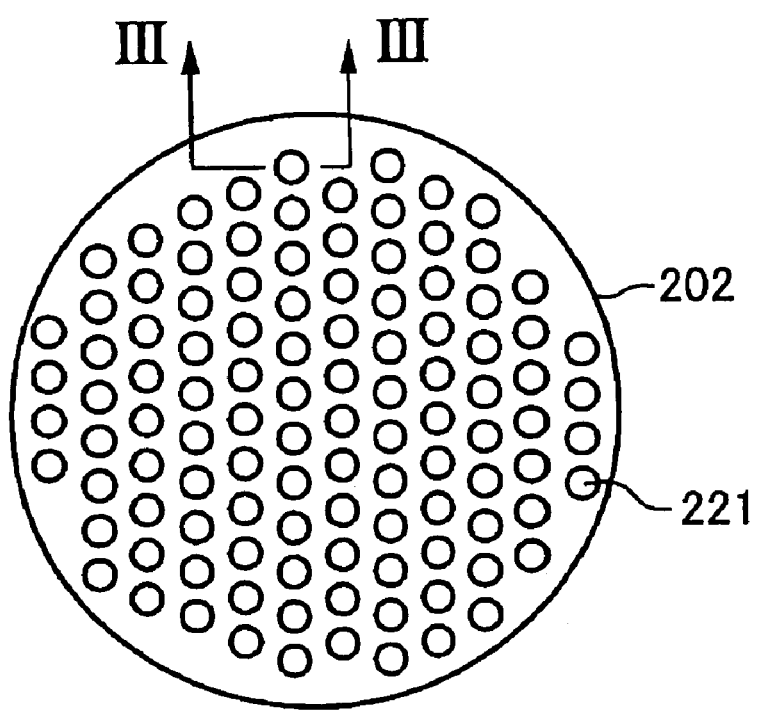
FIG. 10 is a plan view of a perforated tray.
Figure 11:
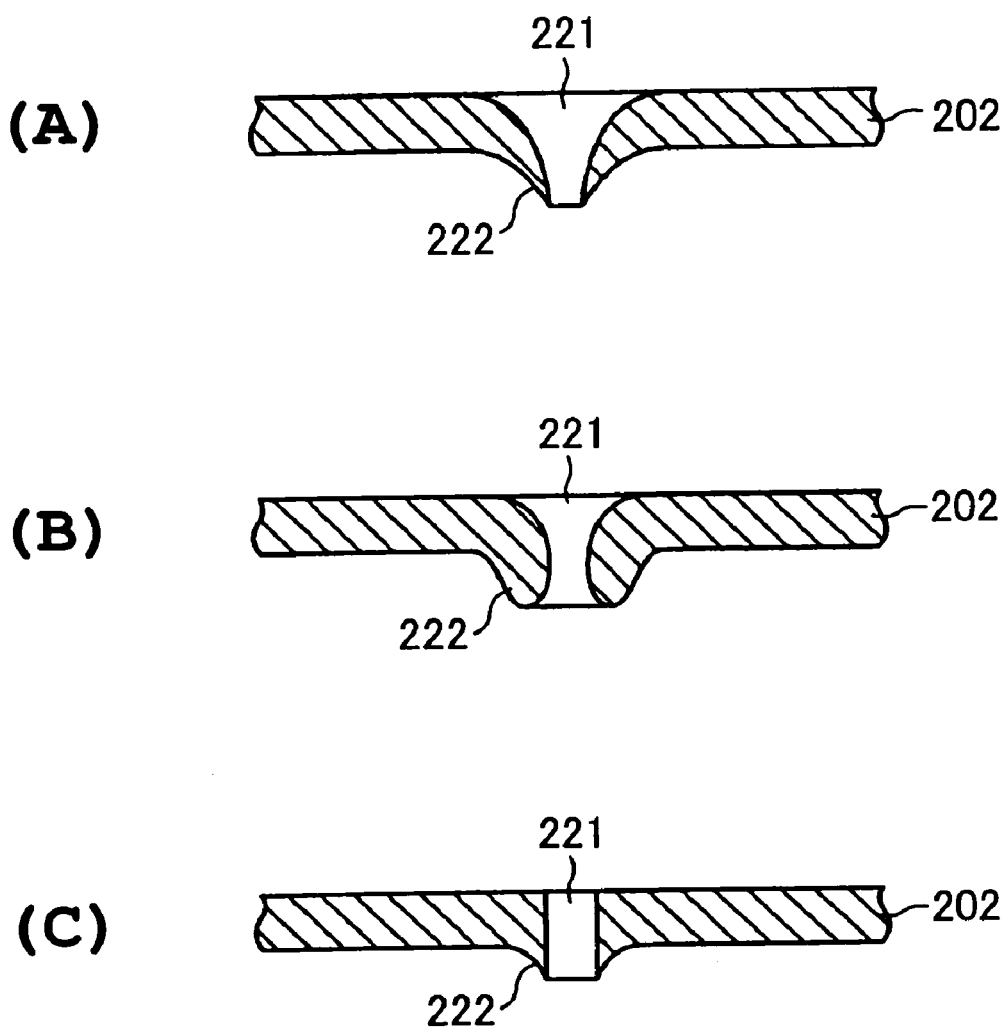
FIG. 11 is a sectional view of each embodiment of a pore in the III-III arrow of FIG. 10.

FIG. 9 is a schematic view of a distillation column; FIG. 10 is a plan view of a perforated tray; and FIG. 11 is a sectional view of each embodiment of a pore in the III-III arrow of FIG. 10. In FIG. 9, 201 is a distillation column, and perforated trays 202 are provided in the plural number of stages at prescribed intervals in the distillation column 201. 203 is a stock liquid feed pipe of a solution containing (meth)acrylic acids, and the stock liquid feed pipe 203 is installed in a position at which the stock liquid is continuously fed on the way in the distillation column 201 where the liquid concentration is proper.

241 is a vapor inlet pipe, and one end of the vapor inlet pipe 241 is connected to the side face in the lower portion of the distillation column 201, the other end thereof being connected to a reboiler 204. Also, 242 is a liquid outlet pipe, and one end of the liquid outlet pipe 242 is connected to the bottom portion of the distillation column 201, the other end thereof being connected to the reboiler 204. A part of the liquid introduced into the liquid outlet pipe 242 is vaporized upon application of heat by the reboiler 204, introduced into the vapor inlet pipe 241, and again returned into the column from the lower side of the distillation column 201. Also, a part of the liquid is introduced into a bottoms pipe 243 connected on the way of the liquid outlet pipe 242 and taken out from the system. 251 is a vapor outlet pipe, and one of the vapor outlet pipe 251 is connected to the column top of the distillation column 201, the other end thereof being connected to a condenser 205. And a part of the liquid condensed in the condenser 205 is introduced into a reflux pipe 252 and again returned into the column from the vicinity of the column top of the distillation column 201, and a part of the liquid is introduced into a distillate pipe 253 and taken out from the system.

In FIG. 10, 202 is a perforated tray, and plural pores 221 penetrating from the upper face of the perforated tray 202 to the back face thereof are provided. The pores 221 have a variety of sectional shapes as shown in FIG. 11(A) to FIG. 11(C).

That is, an example of FIG. 11(A) is concerned with a structure in which the pore size of the pore 221 provided in the perforated tray 202 is gradually reduced from the upper face to the back face, a surrounding projection wall 222 hanging down from the back face of the tray 202 is provided in the outer periphery of the lower end of the pore 221, and the end terminal of the surrounding projection wall 222 is coincident with the end terminal of the inner wall of the pore 221.

Accordingly, the liquid caught on the upper face of the perforated tray 202 smoothly flows into the pore 221, and the liquid flown into the pore 221 flows down from the terminal end of the pore 221.

In that case, the liquid having passed through the pore 221 is prevented from going around into the back face of the perforated tray 202 by the surrounding projection wall 222, whereby the whole of the liquid flows down.

An example of FIG. 11(B) is concerned with a structure in which the pore size of the pore 221 is gradually reduced from the upper face of the perforated tray 202 and again gradually enlarged toward the back face of the tray 202, and a surrounding projection wall 222 hanging down from the back face of the tray 202 is provided in the outer periphery of the lower end of the pore 221.

Accordingly, the liquid caught on the upper face of the perforated tray 202 smoothly flows into the pore 221, and the liquid flown into the pore 221 flows down in a granular form in the state that it is diffused to some extent from the terminal end of the pore 221.

On the other hand, the vapor rising within the distillation column 201 smoothly flows into the pore 221 from the lower end of the pore 221 whose pore size is gradually enlarged and is released upward from the upper face of the perforated tray 202.

In that case, the liquid having passed through the pore 221 is also prevented from going around into the back face of the perforated tray 202 by the surrounding projection wall 222, whereby the whole of the liquid flows down.

An example of FIG. 11(C) is concerned with a structure in which the pore size of the pore 221 is identical from the upper face to the back face of the perforated tray 202, and a surrounding projection wall 222 hanging down from the back face of the tray 202 is provided in the outer periphery of the lower end of the pore 221.

In that case, the liquid having passed through the pore 221 is also prevented from going around into the back face of the perforated tray 202 by the surrounding projection wall 222, whereby the whole of the liquid flows down.

In the pore having such a shape, in boring the pores 221 using a punching press, a drill, etc. from the upper face of the tray to prepare the perforated tray 202, the surrounding projection wall 222 is formed by effectively utilizing a warp inevitably generated in the edge periphery of the pore 221 on the back face of the perforated tray 202. Accordingly, the perforated tray 202 can be cheaply prepared.

When a (meth)acrylic acid is produced using a distillation column in which the perforated tray 202 having a special shape as shown in FIG. 11 is provided in the prescribed number of stages, since the liquid does not go around into the back face of the perforated tray 202, no polymer is formed, and the distillation column can be continuously operated over a long period of time.

The foregoing compound is the major component, and the case where the solvent and reaction by-products set up in various ways in the process are contained is also a subject of the invention.

In the invention, by employing a special structure as the perforated tray to be provided in the distillation column, the readily polymerizable liquid caught on the upper face of the perforated tray passes through the pores provided in the perforated trays, and the whole of the liquid flows downward without causing the matter that a part of the liquid goes around into the back face of the perforated tray.

The invention is quite free from the conventionally occurred phenomenon in which a part of the solution having passed through pores of a perforated tray of this kind goes around into the back face of the tray to form a polymer.

Accordingly, in the invention, in producing a (meth) acrylic acid using a distillation column, it is possible to carry out the operation stably over a long period of time while effectively preventing the formation of a polymer as likely occurred.

In the method of the invention, at least a part of trays is a weir-free perforated tray; openings of the weir-free perforated tray are positioned on respective intersections of an oblique lattice comprising a first group of lines aligned in parallel and at even intervals and a second group of lines oblique to the first group of lines and aligned in parallel and at even intervals; with respect to a local opening rate (B/A) that is a ratio of a sum B of areas of openings of a region comprising of a parallelogram surrounded by the oblique lattice to an area A of the region and a ratio u/S of a total area u of all of the openings to a column sectional area S, a value of (u/S)/(B/A) ratio is 0.67 or more; the flow rate dropping along an edge of the opening is 0.035 $m^3$/m·h or more; the distillation column has a column diameter of 1.2 m or more; and an oxygen concentration in a gas within the column is from 0.008 to 0.1% by mole. Thus, it is possible to distill (meth)acrylic acid stably over a long period of time without causing plugging of the distillation column due to polymerization of (meth)acrylic acid.

The foregoing embodiment of the invention will be described below with reference to the drawing.

Figure 12:
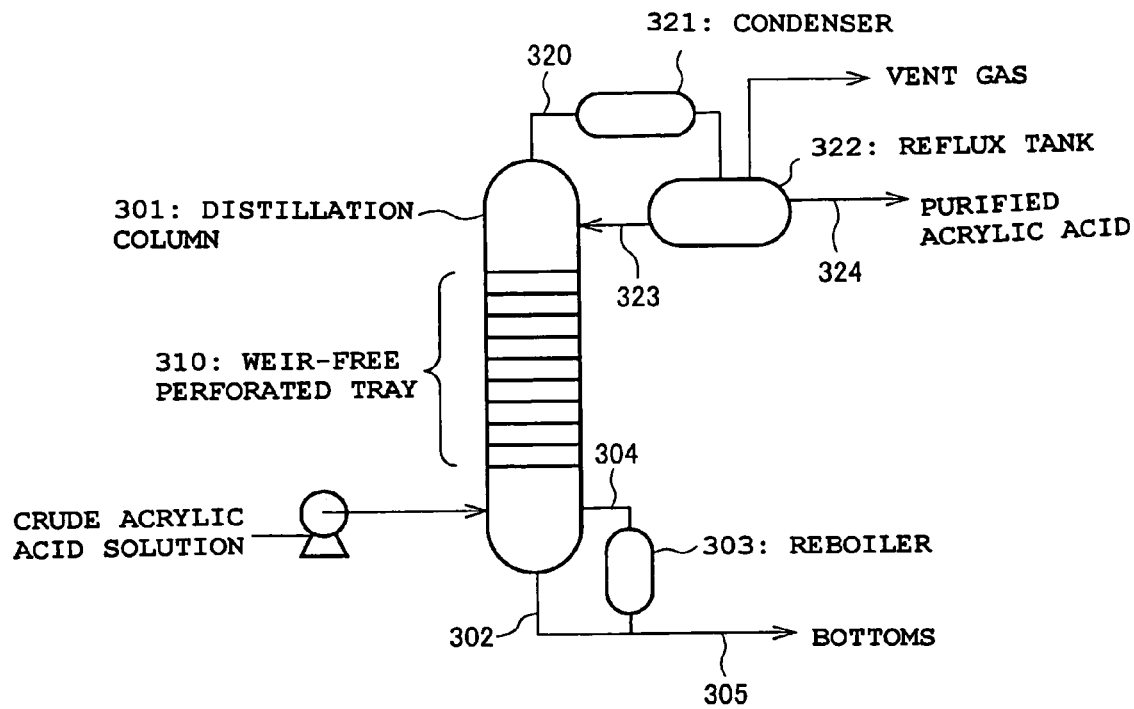
FIG. 12 is a system diagram to show a distillation method of (meth)acrylic acid of the invention.
Figure 13:
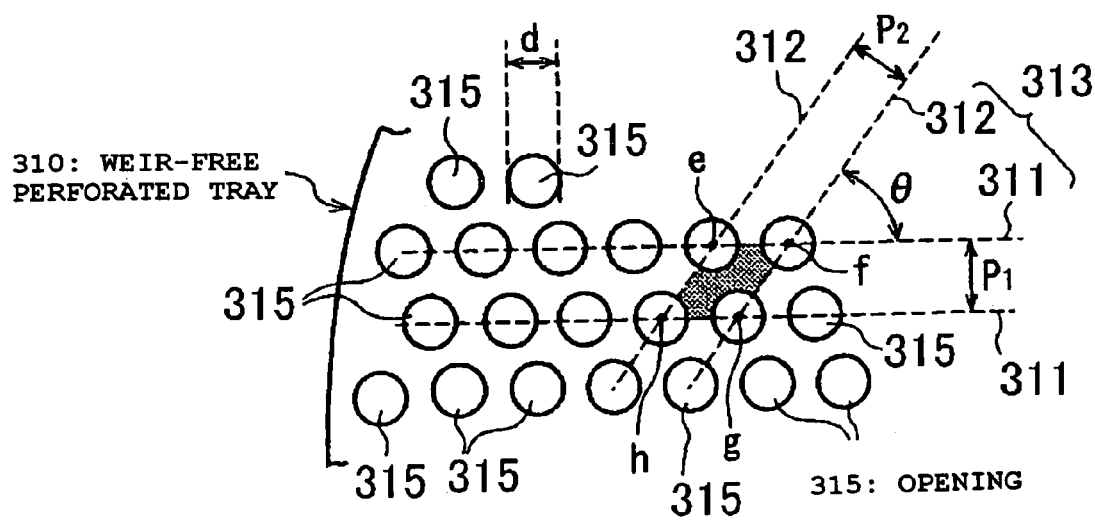
FIG. 13 is an enlarged plan view of a part of a weir-free perforated tray.

FIG. 12 is a system diagram to show a distillation method of (meth)acrylic acid of the invention; and FIG. 13 is an enlarged plan view of a part of a weir-free perforated tray.

As shown in FIG. 12, a crude acrylic acid solution from the production step of acrylic acid is introduced into a distillation column 301 in which a weir-free perforated tray 310 is horizontally provided in the plural number of stages and distilled, and a part of the column bottom liquid is circulated into a conduit 302, a reboiler 303, and a conduit 304 in that order. Also, the column bottom liquid is taken out as bottoms through a conduit 305 connecting to the reboiler 303.

The distillate from the column top is introduced into a reflux tank 322 through a conduit 320 and a condensing condenser 321. A part of acrylic acid in the reflux tank 322 is returned into the column top through a conduit 323. The remainder of acrylic acid is taken out as purified acrylic acid through a conduit 324. The gas in the reflux tank 322 is again cooled in a vent gas condenser (not illustrated), condensed acrylic acid is returned into the reflux tank 322, and the gaseous component is taken out as a vent gas through vacuum equipment.

As shown in FIG. 13, the weir-free perforated tray 310 is provided a number of openings 315. The center of each of the openings 315 is positioned on each of intersections of an oblique lattice 313 comprising a first group 311 of lines aligned in parallel and at even intervals and a second group 312 of lines oblique to the first group of lines and aligned in parallel and at even intervals.

As described later, the opening 315 is preferably circular, and its pore size is preferably from 10 to 30 mm. An interval p1 in the first group 311 of lines is suitably from 35 to 140 mm, and an interval p2 in the second group 312 of lines is suitably satisfied with the relationship of $(1 \leq p2/p1 \leq 2)$. A crossed angle θ between the first group 311 of lines and the second group 312 of lines is suitably satisfied with the relationships of $(\pi/4 \leq \theta \leq \pi/2)$ and $\{\cos-1(p2/p1) \leq \theta\}$. When the openings 315 are aligned at even intervals, the liquid from each of the openings 315 drops down uniformly, whereby a biased flow is prevented, and generation of polymerization by the biased flow is prevented.

A local opening rate defined in terms of a ratio (percentage) [B/A×100%] that is a ratio of a sum B of areas of openings of a region comprising of a parallelogram surrounded by the first group 311 of limes and the second group 312 of lines, i.e., a parallelogram comprising lattice points e, f, g and h of FIG. 13, to an area A of the region is 17% or more, and preferably from 17 to 28%. Incidentally, according to the simple arithmetical computation, A is equal to (p1·p2/sin θ), and B is equal to (π·$d^2$/4). Also, as the whole of trays, a total area u of all of the openings is (π/4·$d^2$×n) (n: total number of pores), and when the inner diameter of the column is defined as D, a column sectional area S is expressed by ($\pi/4 \cdot D2$). At that time, when a value of the (B/A)/(u/S) ratio is set up at 0.67 or more, the flow of the liquid in the column is made uniform, whereby polymerization is prevented.

The amount of the liquid dropping along an edge of each of the openings 315 is desirably 0.035 m³/m·h or more, and especially desirably from 0.04 to 0.25 m³/m·h per unit length (m) and unit time (h) of the edge. When the amount of the liquid is less than 0.035 m³/m·h, accumulation of polymers occurs in the surrounding of the pore, whereby plugging occurs, and a differential pressure of the distillation column increases.

In order that there may be no difference in the flow rate flowing down from the surrounding of the pore, it is desired that the pore sizes are all equal to each other. In the case where the pores having a different pore size are used, the smaller the pore size, the lower the liquid flow rate in the surrounding of the pore is. Accordingly, plugging due to polymerization is liable to occur starting from this pore as a base point, thereby accelerating plugging in the vicinity of the pore whose pore size has become smaller due to the plugging.

With respect to the shape of the pore, a circle in which the length of the surrounding of the pore is longest against the fixed pore area, and the liquid rate flowing down from the surrounding of the pore is not biased is desired. When the pore size d is large, the length of the surrounding of the pore against a fixed pore area becomes small, and the amount of the liquid dropping along the surrounding of the pore per unit length becomes large. However, when the pore size is too large, the stable operation becomes difficult, and therefore, the pore size is desirably not more than 30 mm. Also, when the pore size d is too small, it becomes difficult to secure the liquid flow rate per unit length, and therefore, the pore size is desirably 10 mm or more.

In the case where the column diameter is small, it is preferable that the perforated tray is supported by a support ring (not illustrated) to be placed in the inner periphery of the column. When the column diameter is large, for the sake of keeping mechanical strength, it is preferable that the weir-free perforated tray is supported by a support beam (not illustrated) in addition to the support ring. With respect to the shape, construction, alignment, etc. of the support ring and the support beam, there are no particular limitations. However, in order to make the number of the openings 315 to be covered by the support ring and the support beam small as far as possible, it is preferable that the plane visible areas of the support ring and the support beam are as small as possible. Incidentally, in order to make these areas small while keeping the mechanical strength, for example, there is a method of increasing the tray thickness. In order to make it easy to set up or exchange the weir-free perforated tray, the weir-free perforated tray may be broken up into several pieces.

An interval between the trays is preferably 0.3 m or more from the standpoint of gas rate. However, in order that the column may not become excessively tall, the interval between the trays is preferably not more than 0.75 m.

It is preferable to feed molecular oxygen from the column bottom such that the oxygen concentration in the gas within the column is from 0.008 to 0.1% by mole. It is widely known that oxygen in which an electron spin is in the triplet state in the ground state is excellent as a capturing agent of radicals. Since oxygen is fed as the gas, it is uniformly dispersed over the whole of distillation column. When the oxygen concentration in the gas within the column is lower than 0.008% by mole, an effect for preventing polymerization lowers. On the other hand, when the oxygen concentration within the column exceeds 0.1% by mole, it may possibly accelerate plugging within the column. It is generally considered that in addition to capture of radicals, the molecular oxygen reacts with organic materials in the solution to form peroxides, whereby radicals are formed due to the peroxides.

Though in the foregoing embodiments, all of the perforated trays are made of a weir-free perforated tray, only a part of the perforated trays may be made of a weir-free perforate tray.

According to the process of the invention, a polymerization inhibitor solution is prepared using waste water containing (meth)acrylic acid generated in a vacuum source of the distillation apparatus provided in a preliminary purification step of removing the absorbing liquid and impurities from a (meth)acrylic acid solution obtained in a collection step of an oxidation reaction product mixture to obtain crude (meth)acrylic acid and/or a purification step of distilling (meth)acrylic acid and then fed into the collection step or subsequent steps thereto. Thus, an effect for reducing a purification load in the preliminary purification step becomes enhanced.

The crude (meth)acrylic acid is further purified in the subsequent purification step to obtain (meth)acrylic acid having a desired grade. There are several proposals with respect to the purification method. In any of the methods, (meth)acrylic acid purified by vacuum distillation is obtained as a column top distillate. In the purification step, (meth)acrylic acid may possibly be obtained as an intermediate column top distillate by other vacuum distillation than this vacuum distillation depending upon the process. As the vacuum source of these vacuum distillations, a steam ejector and a liquid ring vacuum pump are generally employed. Now, (meth)acrylic acid that has not been able to be condensed by the condenser of the distillation column, that is, one corresponding to the vapor pressure at the condensation temperature, flows into such a vacuum source. Accordingly, (meth)acrylic acid is dissolved in waste water from the vacuum source such as waste water discharged from the condenser of the steam ejector. However, this waste water does not substantially contain materials as impurities for (meth)acrylic acid.

In the invention, this waste water is used as a solvent of dissolving the polymerization inhibitor. Thus, not only (meth)acrylic acid in the waste water can be recovered as the product, but also a load of the purification system is never increased.

As the polymerization inhibitor that can be used herein, the following compounds are enumerated, but copper carbonate or copper hydroxide is preferable. Copper carbonate or copper hydroxide is insoluble in water but readily soluble in the waste water from the vacuum source. It is considered that copper carbonate or copper hydroxide reacts with dissolved (meth)acrylic acid to form a (meth)acrylic acid salt. The amount of the copper compound to be added to the waste water is arbitrary but is usually from 1 ppm by weight to 10% by weight. Incidentally, in place of the waste water containing (meth)acrylic acid obtained from the vacuum source of the purification step, the vacuum source of the preliminary purification step, such as waste water generated in the vacuum source of a light-boiling distillation column for removing acetic acid and other low-boiling components, can also be used. However, since in addition to (meth)acrylic acid, acetic acid is also dissolved in this waste water, and the concentration of (meth)acrylic acid is usually low, it is preferable to use the waste water of the vacuum source of the purification step as described previously.

The polymerization inhibitor solution prepared using the waste water containing (meth)acrylic acid from the vacuum source is added to the absorbing liquid of mainly collecting the reaction product gas. Thus, by feeding (meth)acrylic acid in the waste water of the vacuum source into the purification system, it is possible to improve the yield of (meth)acrylic acid.

Attendant matters of the invention will be described below.

In the production of acrylic acid or an acrylic acid ester as the readily polymerizable compound, a polymerization inhibitor is used for the sake of retarding the generation of polymers during the production as described previously.

Specific examples of the polymerization inhibitor include copper acrylate, copper dithiocarbamates, phenol compounds, and phenothiazine compounds. Examples of copper dithiocarbamates include copper dialkyldithiocarbamates such as copper dimethyldithiocarbamate, copper diethyldithiocarbamate, copper dipropyldithiocarbamate, and copper dibutyldithiocarbamate; copper cyclic alkylenedithiocarbamates such as copper ethylenedithiocarbamate, copper tetramethylenedithiocarbamate, copper pentamethylenedithiocarbamate, and copper hexamethylenedithiocarbamate; and copper cyclic oxydialkylenedithiocarbamates such as copper oxydiethylenedithiocarbamate. Examples of phenol compounds include hydroquinone, methoquinone, pyrrogallol, catechol, resorcin, phenol, and cresol. Examples of phenothiazine compounds include phenothiazine, bis-($\alpha$-methylbenzyl)phenothiazine, 3,7-dioctylphenothiazine, and bis-($\alpha$-dimethylbenzyl)phenothiazine.

N-Oxyl compounds such as tertiary butyl nitroxide, 2,2,6,6-tetramethyl-4-hydroxypiperidine-1-oxyl, 2,2,6,6-tetramethylpiperidine-1-oxyl, and 4,4',4''-tris-(2,2,6,6-tetramethylpiperidinooxyl)phosphite can also be used. It is preferable to use cheap copper carbonate or copper hydroxide.

Substances other than those described previously may possibly be contained depending upon the process, but it is evident that their kinds do not influence the invention.

The distillation column as referred to in the invention is ones generally employed in the chemical plant. That is, it is provided with an evaporator and a reboiler and if desired, further constructed of a cooling heat exchanger of condensing evaporated gases, a tank of storing a condensate, a pump of delivering a condensate, etc. There are no limitations at all in the invention.

EXAMPLES

Referential Examples 1 and 2 are to specifically explain that by using a distillation apparatus for readily polymerizable compound having a column main body and a reboiler into which a column bottom liquid of the column main body is introduced through an introducing tubular member, the introducing tubular member connecting to the side face of the column main body, plugging of the reboiler can be prevented, and column equipment can be continuously operated stably over a long period of time.

Referential Example 1

Decomposition reaction of a high-boiling liquid was carried out using the decomposition reaction apparatus of FIG. 8.

As the decomposition reaction apparatus, the pipe sizes a and b of the nozzles 102 and 103 are 155.2 mm (6B size), respectively, and (a/b) is equal to 1. A conduit 141 has a pipe size of 106.3 mm (4B size). The decomposition reactor has a column diameter of 1,000 mm and a column length of 2,800 mm and is made of Hastelloy C.

The high-boiling liquid had a formulation consisting of 21% by weight of butyl acrylate, 65% by weight of butyl $\beta$-butoxypropionate, 4% by weight of butyl acryloyloxypropionate, 2% by weight of butyl $\beta$-hydroxypropionate, 3% by weight of hydroquinone, 2% by weight of methoxyquinone, and 3% by weight of others and was fed at a rate of 580 kg/h.

As the reaction conditions, the decomposition reaction was carried out under a reaction pressure of 100 kPa at a decomposition temperature of 190° C. for a residence time of one hour while feeding a 1% by weight aqueous solution of sulfuric acid as a decomposition reaction catalyst in a weight ratio of 10% to the feed liquid.

A decomposition reaction product consisting of 8.7% by weight of butyl acrylate, 62.5% by weight of butyl $\beta$-butoxypropionate, 2% by weight of butyl acryloxypropionate, 0.3% by weight of butyl $\beta$-hydroxypropionate, 8.7% by weight of hydroquinone, 5.8% by weight of methoxyquinone, 0.8% by weight of butanol, 2.9% by weight of sulfuric acid, and 9% by weight of others was obtained at a rate of 200.1 kg/h as a reaction residue from the column bottom and discharged from the column bottom.

The reboiler is a vertical fixed tube type heat exchanger. The amount of the feed liquid to the reboiler was measured by a flow meter placed in the outlet of the pump 140, and an initial value thereof was 32,000 kg/h. The column bottom liquid was passed through the tube side of the reboiler.

Under the foregoing conditions, in the case where an elevation $\theta$ of the introduction nozzle 103 was set up at 45°, after continuous operation for 3 months, the operation was stopped, and the reboiler was inspected. As a result, accumulation did not occur, the amount of the feed liquid to the reboiler was stable, and plugging was not observed during the operation.

In the case where an elevation $\theta$ of the introduction nozzle 103 was set up at 0° (horizontally), after continuous operation for 3 months, the operation was stopped, and the reboiler was inspected. As a result, neither accumulation nor plugging was observed during the operation.

In the case where the introduction nozzle 103 was projected downward in the vertical direction from the lowest portion of the column main body 101, after operation for 2 months, the amount of the feed liquid to the reboiler started to gradually lower. In a hurry, the operation of the decomposition reaction column was stopped. As a result of inspecting the inside, plugging of the pipe of the reboiler was confirmed.

Decomposition reaction of a high-boiling liquid was carried out by changing the formulation of the high-boiling liquid to one consisting of 45.3% by weight of acrylic acid, 10% by weight of maleic acid, 42.4% by weight of an acrylic acid dimer (acryloxypropionic acid), 1.3% by weight of hydroquinone, and 1% by weight of phenothiazine and changing the reaction pressure to 72 kPa so as to obtain a decomposition reaction product consisting of 8% by weight of acrylic acid, 14% by weight of maleic acid, 67.2% by weight of an acrylic acid dimer (acryloxypropionic acid), 5.8% by weight of hydroquinone, 4.4% by weight of phenothiazine, and 0.6% by weight of oligomers and polymers at rate of 130.5 kg/h as a reaction residue from the column bottom.

Under the foregoing conditions, in the case where an elevation θ of the introduction nozzle 103 was set up at 45°, after continuous operation for 3 months, the operation was stopped, and the reboiler was inspected. As a result, accumulation did not occur, the amount of the feed liquid to the reboiler was stable, and plugging was not observed during the operation.

In the case where the introduction nozzle 103 was projected downward in the vertical direction from the lowest portion of the column main body 101, after operation for one month, the amount of the feed liquid to the reboiler started to gradually lower. In a hurry, the operation of the decomposition reaction column was stopped. As a result of inspecting the inside, plugging of the pipe of the reboiler was confirmed.

Referential Example 2

In the distillation apparatus shown in FIG. 7, distillation of crude acrylic acid was carried out using a distillation column made of stainless steel (SUS316) and having an inner diameter of 1,100 mm and a length of 20,000 mm, and having 21 perforated trays (dual trays) set up therein. The pipe sizes of the discharge nozzle 102 and the introduction nozzle 103 were 155.2 mm (6B size), respectively, and a pump was provided on the way of the conduit 104. The conduit 104 has the same size as in the introduction nozzle 103. As the crude acrylic monomer, a mixture containing 98.5% by weight of acrylic acid, 0.3% by weight of maleic acid, and 0.3% by weight of an acrylic acid dimer was fed at a rate of 1,300 kg/h at 90° C.

Also, a solution of acrylic acid having 8% by weight of methoquinone dissolved therein and a solution of acrylic acid having 1% by weight of phenothiazine dissolved therein were fed at a rate of 34 kg/h and 31 kg/h, respectively from the polymerization inhibitor-containing liquid tank, and operation was carried out under a column top pressure of 2.8 kPa and a column bottom pressure of 7.9 kPa at a column top temperature of 53° C. and a column bottom temperature of 75° C., thereby obtaining high-purity acrylic acid having a purity of 99.8% by weight or more from the column top.

The reboiler is a vertical fixed tube type heat exchanger. The amount of the feed liquid to the reboiler was measured by a flow meter placed in the outlet of the pump of the conduit 104, and an initial value thereof was 68,000 kg/h. The column bottom liquid was passed through the tube side of the reboiler.

In the case where an elevation θ of the introduction nozzle 103 was set up at 0° (horizontally), after continuous operation for 6 months, the operation was stopped, and the reboiler was inspected. As a result, accumulation did not occur, the amount of the feed liquid to the reboiler was stable, and plugging was not observed during the operation.

In the case where the introduction nozzle 103 was projected downward in the vertical direction from the lowest portion of the column main body 101, after operation for 4 months, the amount of the feed liquid to the reboiler started to gradually lower. The operation of the decomposition reaction column was stopped. As a result of inspecting the inside, plugging of the pipe of the reboiler was confirmed.

As shown in the foregoing Referential Examples 1 and 2, in any of the decomposition reaction apparatus and the distillation apparatus, by using a distillation apparatus for readily polymerizable compound having a column main body and a reboiler into which a column bottom liquid of the column main body is introduced through an introducing tubular member, the introducing tubular member connecting to the side face of the column main body, the polymers and polymerization inhibitor in the column bottom liquid were retarded from inflow into the reboiler, and plugging of the reboiler was prevented. Thus, it became possible to continuously operate the column equipment stably over a long period of time.

Referential Example 3

The purification method of an acrylic acid solution was carried out in the following manner using the distillation column shown in FIG. 12.

<Preparation Step of Crude Acrylic Acid Solution>

Propylene was mixed with air and an inert gas consisting of water, nitrogen and carbon dioxide, and the propylene was reacted with molecular oxygen in the presence of a molybdenum oxide based solid catalyst in a first reaction zone to obtain acrolein. Subsequently, acrolein was reacted with molecular oxygen in the presence of a molybdenum oxide based solid catalyst in a second reaction zone to obtain a reaction gas containing an acrylic acid. Further, the reaction gas was collected with an acetic acid aqueous solution to obtain an acrylic acid aqueous solution. The resulting solution was subjected to distillation and purification to obtain a crude acrylic acid solution containing. 97% by weight of acrylic acid, 2.3% by weight of an acrylic acid dimer, and 0.4% by weight of maleic acid.

<Distillation Column>

A distillation column as a standard has a column diameter of 1,600 mm and has 10 stages of a weir-free perforated tray therein, in which an interval between the trays is 450 mm. The pore sizes d of the perforate trays are all 28 mm, p1 and p2 are equal to 50.2 mm, respectively, θ is equal to π/3, the number of pores of each tray is 492, and the value of (B/A)/(u/S) is 0.71.

<Purification Conditions>

As the purification conditions as a standard, an acrylic acid solution was fed at a rate of 3,800 kg/h into the column bottom of the foregoing distillation column, and operation was continuously carried out for one month under the conditions of a column top pressure of 6.7 kPa, a column top temperature of 70° C., a reflux rate of 3,850 kg/h and a discharge rate from the column top of 3,050 kg/h. A polymerization inhibitor was fed from the column top such that 100 ppm by weight of hydroquinone and 30 ppm by weight of phenothiazine were contained in the reflux liquid. Air diluted three times with nitrogen gas was fed from the column bottom such that the oxygen concentration in the column top gas was 0.01% by mole.

The operation was carried out by changing the foregoing distillation column and/or the foregoing purification conditions. The following change points are changes from the foregoing distillation column and purification conditions as the standards.

Under the foregoing purification conditions, the amount of the liquid flowing down along the edge of the opening was 0.089 $m^3/m·h$, and a change in differential pressure within the column [(column top pressure)−(column bottom pressure)] was not observed during the operation period. Subsequently, the reflux rate was decreased to 1,600 kg/h, and continuous operation was further carried out for one month. During this period, the amount of the liquid flowing down along the edge of the opening was 0.037 $m^3/m·h$, and a change in differential pressure within the column was not observed during the operation period.

With respect to the foregoing purification conditions, the reflux rate was set up at 1,100 kg/h, and operation was carried out. During this period, the amount of the liquid flowing down along the edge of the opening was 0.025 m$^3$/m·h, and an increase in differential pressure within the column of 0.8 kPa was observed during the operation period of one month.

With respect to the foregoing distillation column, four stages of the trays from the bottom were changed to one in which the pore size is 20 mm, p1 and p2 are equal to 36.3 mm, respectively, θ is equal to π/3, and the number of pores on each tray is 964; and with respect to the purification conditions, the reflux rate was set up at 3,300 kg/h. The value of (B/A)/(u/S) is 0.73. During the continuous operation of one month, with respect to the column bottom tray, the amount of the liquid flowing down along the edge of the opening was 0.054 m$^3$/m·h, and a change in differential pressure within the column was not observed during the operation period.

With respect to the foregoing distillation column, four stages of the trays from the bottom were changed to one in which the pore size is 20 mm, p1 and p2 are equal to 36.3 mm, respectively, θ is equal to π/3, and the number of pores on each tray is 964; and with respect to the purification conditions, the reflux rate was set up at 1,600 kg/h, and the period of continuous operation was set up at 10 days. During the operation, with respect to the column bottom tray, the amount of the liquid flowing down along the edge of the opening was 0.026 m$^3$/m·h, and the differential pressure within the column was increased by 2 kPa.

With respect to the foregoing distillation column, four stages of the trays from the bottom were changed to one in which the pore size is 12 mm, p1 and p2 are equal to 21.6 mm, respectively, θ is equal to π/3, and the number of pores on each tray is 2,664; and with respect to the purification conditions, the reflux rate was set up at 3,850 kg/h. The value of (B/A)/(u/S) is 0.71. During the continuous operation of one month, with respect to the column bottom tray, the amount of the liquid flowing down along the edge of the opening was 0.038 m$^3$/m·h, and an increase in differential pressure within the column was slightly observed (less than 0.2 kPa).

With respect to the foregoing distillation column, four stages of the trays from the bottom were changed to one in which the pore size is 12 mm, p1 and p2 are equal to 21.6 mm, θ is equal to π/3, and the number of pores on each tray is 2,664; and with respect to the purification conditions, the reflux rate was set up at 2,200 kg/h, and the period of continuous operation was set up at 6 days. During the operation, with respect to the column bottom tray, the amount of the liquid flowing down along the edge of the opening was 0.022 m$^3$/m·h, and the differential pressure within the column was increased by 2 kPa.

With respect to the foregoing distillation column, four stages of the trays from the bottom were changed to one in which the pore size d is 28 mm, p1 and p2 are equal to 39.8 mm, respectively, θ is equal to π/3, and the number of pores on each tray is 812; and with respect to the purification conditions, the reflux rate was set up at 3,300 kg/h. The value of (B/A)/(u/S) is 0.74. During the continuous operation of one month, with respect to the column bottom tray, the amount of the liquid flowing down along the edge of the opening was 0.046 m$^3$/m·h, and a change in differential pressure within the column was not observed.

With respect to the foregoing distillation column, four stages of the trays from the bottom were changed to one in which the pore size d is 28 mm, p1 and p2 are equal to 39.8 mm, respectively, θ is equal to π/3, and the number of pores on each tray is 812; and with respect to the purification conditions, the reflux rate was set up at 1,600 kg/h. During the continuous operation of one month, with respect to the column bottom tray, the amount of the liquid flowing down along the edge of the opening was 0.022 m$^3$/m·h, and an increase in differential pressure within the column of 11 kPa was observed.

With respect to the foregoing distillation column, four stages of the trays from the bottom were changed to one in which the pore size is 20 mm, p1 and p2 are equal to 28.5 mm, respectively, θ is equal to π/3, and the number of pores on each tray is 1,604; and with respect to the purification conditions, the reflux rate was set up at 3,850 kg/h. The value of (B/A)/(u/S) is 0.75. During the continuous operation of one month, with respect to the column bottom tray, the amount of the liquid flowing down along the edge of the opening was 0.038 m$^3$/m·h, and an increase in differential pressure within the column of 0.3 kPa was observed.

With respect to the foregoing distillation column, four stages of the trays from the bottom were changed to one in which the pore size is 20 mm, p1 and p2 are equal to 28.5 mm, respectively, θ is equal to π/3, and the number of pores on each tray is 1,604; and with respect to the purification conditions, the reflux rate was set up at 1,600 kg/h, and the operation period was set up at 3 weeks. During the operation, with respect to the column bottom tray, the amount of the liquid flowing down along the edge of the opening was 0.016 m$^3$/m·h, and the differential pressure within the column was increased by 2 kPa.

With respect to the foregoing purification conditions, air diluted three times with nitrogen was fed from the column bottom such that the oxygen concentration in the column top gas was 0.005% by mole, the reflux rate was set up at 2,200 kg/h, and the operation period was set up at 2 weeks. During the continuous operation, with respect to the column bottom tray, the amount of the liquid flowing down along the edge of the opening was 0.051 m$^3$/m·h, and the differential pressure within the column was increased by 1.6 kPa.

With respect to the foregoing purification conditions, air was fed from the column bottom such that the oxygen concentration in the column top gas was 0.12% by mole, the reflux rate was set up at 2,200 kg/h, and the operation period was set up at 2 weeks. During the continuous operation, the differential pressure within the column was increased by 0.7 kPa.

With respect to the foregoing distillation column, four stages of the trays from the bottom were changed to one in which the pore size d is 28 mm, p1 and p2 are equal to 45.8 mm, respectively, θ is equal to π/3, and the number of pores on each tray is 488; and with respect to the purification conditions, the reflux rate was set up at 2,200 kg/h, and the operation period was set up at 2 weeks. The value of (B/A)/(u/S) is 0.59. During the continuous operation, with respect to the column bottom tray, the amount of the liquid flowing down along the edge of the opening was 0.051 m$^3$/m·h, and the differential pressure within the column was increased by 0.3 kPa.

As is clear from the foregoing, by using the specific distillation column and purification conditions of the invention, the effect in which distillation of (meth)acrylic acid can be carried out stably over a long period of time without causing plugging due to polymerization becomes more advantageous.

Referential Example 4

Figure 14:
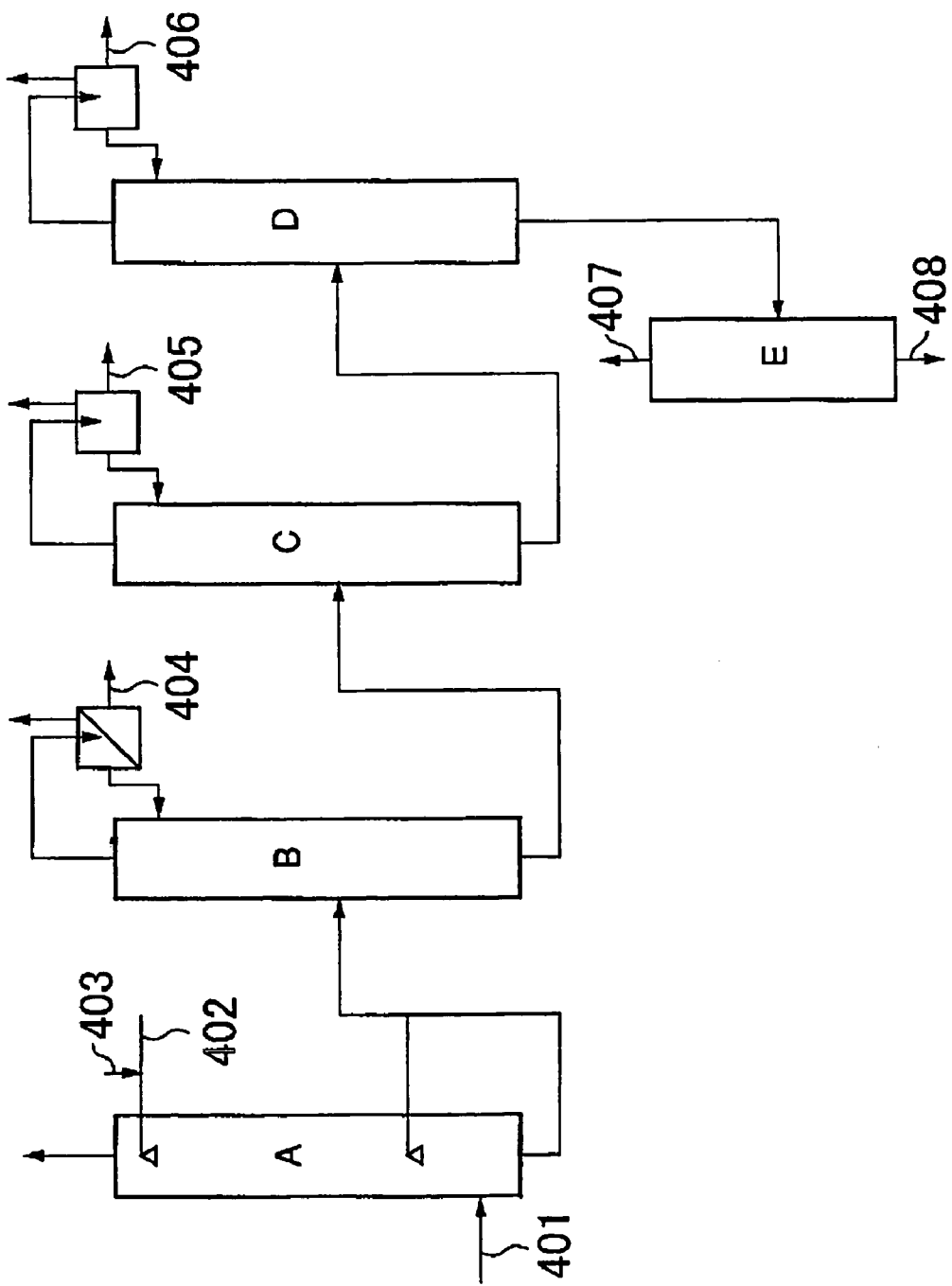
FIG. 14 is one example of a flow sheet of a production process of acrylic acid.

Taking as an example the case of obtaining purified acrylic acid from a reaction product gas containing acrylic acid obtained by vapor phase catalytic oxidation reaction of propylene using an apparatus comprising a collection column (A), a dehydration column (B), a light-boiling removal column (C), a purification column (D), and a heat decomposition column (E) as shown in FIG. 14, it will be more specifically described that when a polymerization inhibitor solution is prepared using (meth)acrylic acid-containing waste water generated in a vacuum source in a preliminary purification step and/or a purification step and fed into the collection step or subsequent steps thereto, a purification load in the preliminary purification step can be reduced.

A reaction product gas is fed into the collection column (A), and about 0.6 kg of water against 1 kg of acrylic acid in the gas is flown down from the column top, thereby absorbing acrylic acid therein. An acrylic acid solution containing about 1.7 kg of acrylic acid based on one liter of water is discharged from the collection column (A) and fed into the dehydration column (B). Also, a polymerization inhibitor solution is fed into the collection column so as to keep the concentration of the polymerization inhibitor at a fixed level. In the dehydration column (B), azeotropic distillation is carried out using an azeotropic agent; the gas flown out from the column top is condensed in a condenser; the condensate is subjected to phase separation; water is exhausted out the system; and the azeotropic agent is returned into the column. The column bottom liquid of the dehydration column is then fed into the light-boiling removal column (C) and distilled in vacuo, thereby distilling substantially the whole of components having a boiling point lower than acetic acid and other acrylic acid. It is preferable that this distillation is usually carried out under a lightly reduced pressure such that acrylic acid does not distil as far as possible. The column bottom liquid of the light-boiling removal column (C) is fed into the purification column (D), thereby distilling acrylic acid purified upon distillation in vacuo under a column top pressure of from 20 to 30 mmHg. A steam ejector is used as a vacuum source of the purification column (D).

The column bottom liquid of the purification column (D) is fed into the heat decomposition column (E), and a light-boiling fraction containing acrylic acid distilling from the column top is fed into the light-boiling removal column (C), thereby exhausting heavy components out the system. In the case of producing acrylic acid purified in a production amount of 10,000 kg/Hr in the foregoing process, when a polymerization inhibitor solution prepared by dissolving 6,000 ppm by weight of cupric carbonate or manganese acetate and 5% by weight of hydroquinone in condensed water (acrylic acid concentration: 10% by weight) of the steam ejector as the vacuum source of the purification column (D) was fed at a rate of 400 kg/Hr into the collection column (A), the yield of purified acrylic acid was 96.6% against acrylic acid in the reaction product gas.

Separately, in the case where a polymerization inhibitor solution prepared by dissolving 6,000 ppm by weight of cupric carbonate or manganese acetate and 5% by weight of hydroquinone in waste water (acetic acid concentration: 10% by weight) obtained from the column top of the dehydration column was fed at a rate of 400 kg/Hr, the yield of purified acrylic acid was 96.1%.

While the invention has been described in detail and with reference to specific embodiments thereof, it will be apparent to one skilled in the art that various changes and modifications can be made therein without departing from the spirit and scope thereof.

This application is based on a Japanese patent application filed Aug. 22, 2001 (Japanese Patent Application No. 2001-251067), a Japanese patent application filed Nov. 27, 2001 (Japanese Patent Application No. 2001-360436), a Japanese patent application filed Dec. 4, 2001 (Japanese Patent Application No. 2001-370271), a Japanese patent application filed Dec. 27, 2001 (Japanese Patent Application No. 2001-397463), and a Japanese patent application filed Jan. 11, 2002 (Japanese Patent Application No. 2002-004318), the contents of which are incorporated herein by reference.

INDUSTRIAL APPLICABILITY

According to the invention, in the method of distilling a crude readily polymerizable compound under vacuum conditions to purity it, an improvement is made such that plugging of a pressure control valve is prevented and the readily polymerizable compound carried in an exhaust gas of a vacuum generator can be easily recovered. Thus, an industrial value of the invention is remarkable.

Further, according to the invention, by employing a structure having a distillation column main body and a reboiler into which a column bottom liquid of the column main body is introduced through an introducing tubular member, the introducing tubular member connecting to the side face of the column main body, effects for preventing plugging of the reboiler and continuously operating column equipment stably over a long period of time are enhanced.

The invention claimed is:

1. A distillation apparatus for subjecting a crude readily polymerizable compound to distillation under vacuum conditions to purify the same, the apparatus comprising:
   a distillation column;
   a reflux tank having an inlet, an outlet and a vapor phase connecting port, the outlet being connected to the distillation column;
   a condenser having a condensing fluid inlet and a condensing fluid outlet, the condensing fluid inlet being supplied with fluid from the distillation column and the condensing fluid outlet being connected to the reflux tank inlet;
   a vacuum generator connected to the vapor phase connecting port of the reflux tank through an exhaust gas conduit of the vacuum generator;
   a pressure control valve connected to the exhaust gas conduit of the vacuum generator; and
   a pressure controller connected to the pressure control valve, the pressure controller having a pressure detection line.

2. The apparatus according to claim 1, wherein the apparatus has a distillation column main body and a reboiler into which a column bottom liquid of the column main body is introduced through an introducing tubular member, the introducing tubular member connecting to the side face of the column main body.

3. The apparatus according to claim 2, wherein the column main body is provided with a pot part projecting downward in the lower end thereof, and the introducing tubular member connects to the side face of the pot part.

4. The apparatus according to claim 2, wherein a tubular member for discharging a column bottom liquid is projected downward from the lower end of the column main body, and the introducing tubular member connects to the side face of the discharging tubular member.

5. The apparatus according to claim 4, wherein a ratio (a/b) of a pipe size a of the discharging tubular member to a pipe size b of the introducing tubular member is 0.5 or more.

6. The apparatus according to claim 2, wherein a vicinity of an upstream end of the introducing tubular member is horizontal or ascends toward a downstream side.

7. The apparatus according to claim 1, further comprising:
a perforated tray with a number of pores penetrating from an upper face of the tray to a back face thereof, and a surrounding projection wall hanging down from the back face of the tray is provided in the outer periphery of the lower end of the pores is used, the perforated tray being disposed inside the distillation column.

8. The apparatus according to claim 7, wherein the perforated tray is a weir-free perforated tray, openings of the weir-free perforated tray are positioned on respective intersections of an oblique lattice comprising a first group of lines aligned in parallel at even intervals and a second group of lines oblique to the first group of lines and aligned in parallel at even intervals with respect to a local opening rate (B/A) that is a ratio of a sum B of areas of openings of a region comprising a parallelogram surrounded by the oblique lattice to an area A of the region and a ratio u/S of a total area u of all of the openings to a column sectional area S, a value of (u/S)/(B/A) ratio is 0.67 or more, a flow rate dropping along an edge of the opening is 0.035 m3/m·h or more, the distillation column has a column diameter of 1.2 m or more, and an oxygen concentration in a gas within the distillation column is from 0.008 to 0.1% by mole.

9. The apparatus according to claim 8, wherein the opening is a circle having a diameter of from 10 to 30 mm, and when an interval of the first group of lines is defined as p1, an interval of the second group of lines is defined as p2, and an internal angle taken by the first group of lines and the second group of lines is defined as $\theta$, relationships of $(1 \leq p2/p1 \leq 2)$ and $\{\cos^{-1}(p2/2p1) \leq \theta \leq \pi/2\}$ (wherein $\theta \geq \pi/4$) are satisfied.

10. The apparatus according to claim 8, wherein the value of (B/A) is from 0.17 to 0.28, and the value of (u/S)/(B/A) is from 0.67 to 0.90.

11. The apparatus according to claim 1, wherein the vacuum generator is a steam driven ejector, and the readily polymerizable compound is (meth)acrylic acid.

12. The apparatus according to claim 1, wherein the pressure detection line of the pressure controller is connected to a fluid line connecting the distillation column to the condenser.

13. The apparatus according to claim 1, wherein the pressure detection line of the pressure controller is connected to the reflux tank.

14. The apparatus according to claim 1, further comprising:
a supply of a polymerization inhibitor solution prepared using waste water containing (meth)acrylic acid generated in a vacuum source of the distillation apparatus.

* * * * *